(12) United States Patent
Wu

(10) Patent No.: US 10,328,363 B2
(45) Date of Patent: *Jun. 25, 2019

(54) BIOREACTOR SYSTEM AND METHOD

(71) Applicant: Xianggen Wu, Mississauga (CA)

(72) Inventor: Xianggen Wu, Mississauga (CA)

( * ) Notice: Subject to any disclaimer, the term of this patent is extended or adjusted under 35 U.S.C. 154(b) by 164 days.

This patent is subject to a terminal disclaimer.

(21) Appl. No.: 15/615,820

(22) Filed: Jun. 6, 2017

(65) Prior Publication Data

US 2017/0354906 A1 Dec. 14, 2017

Related U.S. Application Data

(63) Continuation-in-part of application No. 15/178,261, filed on Jun. 9, 2016, now Pat. No. 9,617,191.

(51) Int. Cl.
*B01F 3/04* (2006.01)
*B01F 5/00* (2006.01)
(Continued)

(52) U.S. Cl.
CPC ........ *B01D 21/245* (2013.01); *B01F 3/04049* (2013.01); *B01F 7/00158* (2013.01); *B01F 7/00541* (2013.01); *B01F 7/00641* (2013.01); *C02F 3/1268* (2013.01); *C05F 17/027* (2013.01); *C05F 17/0258* (2013.01); (Continued)

(58) Field of Classification Search
CPC ....... B01D 21/245; B01D 63/00; E21B 43/16; E21B 43/34; B01F 7/00158; B01F 7/00541; B01F 7/00641; B01F 3/04049; B01F 2005/0017; C05F 17/0258; C05F 17/027; C05F 17/0282; C12M 23/34; C12M 27/08; C12M 29/06; C12M 37/02; C02F 3/1268; C02F 1/00; C02F 2209/02; Y02P 20/145; Y02W 30/43

See application file for complete search history.

(56) References Cited

U.S. PATENT DOCUMENTS

| | | | |
|---|---|---|---|
| 4,008,689 A * | 2/1977 | Albers | C02F 3/28 119/450 |
| 4,262,633 A * | 4/1981 | Taboga | A01K 67/0332 119/6.7 |

(Continued)

*Primary Examiner* — Gautam Prakash

(57) ABSTRACT

The present invention is a composting bioreactor system that continually receives biodegradable solid wastes, waste waters and exhaust gases, automatically recycles the biodegradable wastes into nutrients and heat energy, and automatically supplies the nutrients and heat into an integrated hydroponic or aquaponic system. This invention together with integrated food growing system may be installed onsite such as balconies, backyards and premises of restaurants and food factories etc. therefore may lead to zero mileage targets both for recycling wastes and for supplying foods. This invention integrates composting process and aquaponic technology together and may establish a closed-loop recirculation of both water and gases therefore upgrades aquaponics into compoponics. A compoponic system has both soil and soilless growing beds and mimics nature recirculating nutrients, carbon and energy among human being, animals, microorganisms and plants by way of photosynthesis, slow burning by cellular respiration and burning by combustion.

20 Claims, 15 Drawing Sheets

(51) Int. Cl.
    *B01F 7/00* (2006.01)
    *C02F 1/00* (2006.01)
    *C02F 3/12* (2006.01)
    *C12M 1/00* (2006.01)
    *C12M 1/06* (2006.01)
    *C12M 1/12* (2006.01)
    *B01D 21/24* (2006.01)
    *B01D 63/00* (2006.01)
    *C05F 17/02* (2006.01)
    *E21B 43/16* (2006.01)
    *E21B 43/34* (2006.01)

(52) U.S. Cl.
    CPC ......... *C05F 17/0282* (2013.01); *C12M 23/34* (2013.01); *C12M 27/08* (2013.01); *C12M 29/06* (2013.01); *C12M 37/02* (2013.01); *E21B 43/16* (2013.01); *E21B 43/34* (2013.01); *B01D 63/00* (2013.01); *B01F 2005/0017* (2013.01); *C02F 1/00* (2013.01); *C02F 2209/02* (2013.01); *Y02P 20/145* (2015.11); *Y02W 30/43* (2015.05)

(56) References Cited

U.S. PATENT DOCUMENTS

| | | | | |
|---|---|---|---|---|
| 5,169,782 A * | 12/1992 | Murphy et al. | ........ | B01F 9/0007 435/290.3 |
| 5,899,568 A * | 5/1999 | Vonnahme | .......... | B01F 7/00158 366/325.1 |
| 5,942,022 A * | 8/1999 | Bislev et al. | ....... | C05F 17/0045 71/9 |
| 6,352,855 B1 * | 3/2002 | Kerouac | .............. | C05F 17/0018 435/290.3 |
| 6,766,592 B1 * | 7/2004 | Clark | ........................ | C05F 3/00 34/186 |
| 6,896,804 B2 * | 5/2005 | Haerther et al. | .......... | C02F 3/32 210/602 |
| 6,996,918 B2 * | 2/2006 | Bsirske et al. | .......... | C02F 1/722 34/265 |
| 7,510,649 B1 * | 3/2009 | Lavigne | .................. | C02F 3/046 137/883 |
| 2006/0060525 A1 * | 3/2006 | Hoffland | ............ | B01D 21/0012 210/603 |
| 2009/0209025 A1 * | 8/2009 | Goschl et al. | ........ | C02F 3/2873 435/262.5 |
| 2009/0230040 A1 * | 9/2009 | Limcaco | .................. | C02F 3/082 210/151 |

* cited by examiner

Wherein in each of the four quarters of the largest circle O:

Oa=Oe
oa=od (ab-cd)/ab
=ed/ab
=ab/Oa
=Oa/Ob
=0.618

The four small equal circles along the segment ab exactly fit the given spaces and are used for curving the blade edges.

BIOREACTOR SYSTEM AND METHOD

CROSS-REFERENCE TO RELATED APPLICATION

The present application is a continuation-in-part application of U.S. patent application Ser. No. 15/178,261 filed on Jun. 9, 2016, now U.S. Pat. No. 9,617,191.

FIELD OF THE INVENTION

This invention relates to systems for treatment of biodegradable wastes by way of aerobic decomposition. More specifically, this invention relates to composting bioreactor systems that can be continually fed with biodegradable solid wastes, waste waters, and exhaust gases and that automatically recycle the fed wastes into nutrients and heat to grow foods. This invention integrates the composting process with the aquaponic technology together therefore upgrades aquaponics into compoponics.

BACKGROUND OF THE INVENTION

Biodegradable waste is the type of waste that can be broken down by way of composting (aerobic decomposition and anaerobic decomposition) into base compounds (H2O, CO2, compounds of Nitrogen, Phosphorus, Potassium and others), energy (heat) and residual humus. The residual humus can eventually break down into fine particles and can be automatically transported by water circulation.

Both the aerobic decomposition and the anaerobic decomposition belong to the biological process of cellular respiration, also called the slow burning. Microorganisms such as bacteria, fungi and protozoa as well as animals such as earthworm and fly larvae are all players in the composting process by way of cellular respiration. Broadly speaking, biodegradation also includes another nature process, the burning by combustion that transforms biomasses into H2O, CO2, light energy, heat energy, ash and other exhaust gases. Photosynthesis is the nature process that transforms CO2, H2O and other nutrients into biomasses by use of solar energy.

Biodegradable wastes are produced in huge volume from human activities. They include solid wastes such as kitchen food waste and backyard plant waste as well as packaging waste (papers, cartons and wood pallets etc.), waste waters such as from sinks of kitchen and from sinks, showers, bathtubs as well as toilets of bathroom, and exhaust gases such as from furnace vent and stove vent. Households and IC/I (industrial, commercial and institutional) entities, etc. are all producers of the wastes.

It is a labour burden task to collect the wastes from households and IC/I entities and to transport them into municipal treatment centers. Producers of the wastes also need to spend time and labor to get them ready for collection. Greenhouse gas emission from transport of the wastes and their recycled result products is one of the inputs leading to climate change. It costs a lot of money from both private and public in building and maintaining urban sewage piping systems for transporting waste waters into municipal treatment centers. Exhaust gases from households and industries discharged directly into atmosphere without treatment increase air pollutions.

Recycling the above wastes in the municipal treatment centers by way of composting, incineration or landfill etc. can recover some part of the beneficial ingredients from the wastes treated, but also pollutes the atmosphere, soil and even groundwater. Furthermore, it also needs large lands and costs a lot in building and maintaining the treatment utilities.

A lot of efforts have been made in addressing onsite treatment of the biodegradable wastes. Composters including vermi-composters that use natural ventilation are not in a sealed vessel therefore let go heat, odors and exhaust gases into the atmosphere.

The U.S. Pat. No. 5,744,351 to Michael Bryan-Brown discloses a bioreactor for aerobically composting organic waste inside a sealed container. It integrates a mixing assembly and an aeration system so that the inside composting wastes can be well ventilated. However, this design type needs to manage the exhaust gases by way of a bio-filter and to manage the leachate liquid by use of a pump.

The patent application No. CN101823069 by Aimin Li et al discloses an auto-controlled composter with ventilation and heat components to promote the composting process inside a vessel. Again, it still needs components to filter the exhaust gases and to manage the leachate liquid.

Both the above composters are designed for the purpose to recycle the bio wastes into compost only. The bio wastes are fed by batch into the composter, after certain time the completed compost is to be discharged and transported. Pollutants to environment can be disposed from exhaust gases, leachate liquid and completed compost. Nutrients of the bio wastes and heat from the composting wastes are not fully utilized. When these composters are employed, the bio wastes inside the vessel of a batch undergo all composting stages, therefore in each stage the quantity of microorganisms reaches its highest point and then decreases or even disappears in a later stage because of changed conditions. When the complete compost of a batch is discharged, the microorganisms inside the composter are also discharged. It is a totally new process for microorganisms to grow into large quantities during the new composting stages of the newly fed batch of bio wastes.

It is desirable that the biodegradable wastes be composted onsite within its source location with the completed compost locally used with zero mile of transportation, with zero pollution to the environment from the composting process, and with all the nutrients and heat energy from the wastes fully recovered and reused. It is also desirable that the condition of microorganisms stay unchanged when the biodegradable wastes undergo each of the composting stages.

In response to the growth of demand for healthy foods available in minimum mileage, the hydroponic technology and the aquaponic technology have been in practice for decades. When these practices happen in the household backyard or in the food consume premises, zero food mileage can be achieved as regard to the foods produced and consumed in the same location.

However, the conventional hydroponic system needs to add artificial nutrients into its circulating water to feed plants. In a typical aquaponic system fish feed is from outside source, and the waste water from integrated fishing tanks doesn't have enough nutrients to support the growing plants, therefore minerals and other nutrients have to be added. Furthermore, a filter and a bioreactor are required to separate and to degrade solid wastes in the waste water from the aquaponic fish tanks.

Compost tea is one of the options to supply nutrients to plants in the hydroponic and aquaponic systems. Compost tea is produced by putting a bag of compost into a vessel with aerated water for certain time to allow microbes grow. It is nutritious for growing plants and therefore good to be added into the hydroponic and aquaponic systems. Different devices are available but are separately operated from the hydroponic and aquaponic systems.

Although it is valuable to grow short mileage foods with little water loss by way of the hydroponic system or the aquaponic system, their values are limited by the high start-up costs comparing to the volume of foods produced, for they are used to grow foods only. The system does not automatically recycle waste biomass produced from itself and from other sources. Another concern is quality of the soilless cultured foods. Some food plants don't fit for soilless culture, while quality of soilless cultured foods may be different from soil cultured foods.

It is desirable to have a bioreactor system that can be integrated into the hydroponic system or the aquaponic system, which can onsite automatically recycle biodegradable wastes into nutrient liquid to feed the growing plants, and that can also grow feed for the aquarium animals. Furthermore, it is desirable to have a bioreactor system that can be integrated into the food growing systems, that can automatically recycle all the biodegradable wastes including solid wastes, waste waters and exhaust gases from both the food production sources and from the onsite human activities, and that can fully recover nutrients and heat energy from the treated wastes to grow foods with zero pollution to the environment. It is also desirable that soil growing beds may be integrated into the food growing system so that most kinds of food plants can be cultured in an integrated system.

The patent application No. CA2759981A1 by Nicholas Hermes and James Sawada discloses a food production system that composts biomass and uses the completed compost to grow foods with heat and nutrients recovery. In this system biomasses are fed by batch mode to a composter and then physically transferred into another invertebrate culture unit and lastly transferred into a food culture unit. The heat recovery is carried by way of a complicated pipe system which circulates heat exchange liquid. In this design, the biomass is not kept inside of a sealed vessel during all processes; pollutants to environment can be disposed from the exhaust gases while nutrients and heat are not fully recovered.

In the prior art composters that can be employed onsite of the waste source, the biomasses or the bio wastes or the organic wastes or the biodegradable wastes that can be fed into the composter, have numerous limitations. The wastes such as wood pallets, tree trunks and branches of large size are usually not acceptable. The present invention provides an onsite biomass composting and reuse, which overcomes the limitations of the prior art.

One of the important steps for sealed in-vessel composting is to mix or agitate the inside contents so that all the volume is well aerated. Either a slow speed motor that rotates the whole vessel/drum or a fast speed motor that drives an agitator to cause movements of the whole volume is usually employed. In the U.S. Pat. No. 5,744,351, a vertically installed slidable mixing assembly is employed so that almost all the inside volume can be reached for agitation. This method requires a worker to manually operate the mixing assembly. In the patent application CN101823069, a mixing module is horizontally installed and it horizontally rotates the whole volume inside the vessel. All these methods are not efficient in comparing the power energy required with the simple aeration resulted.

The traditional plow, especially the chisel plow is typically much more efficient in comparing the power required with the volume of mass (soil) moved or agitated. Inside a sealed vessel, if some part of the contents along the bottom layer is physically moved, it can cause somewhat movements of the whole contents. This kind of movements are good enough for aeration of the whole volume, especially if the air is from a space below the volume. Desirably a very slow speed movement caused by rotating a chisel plow type agitator can well aerate the whole volume.

Also, most prior art agitators for in-vessel liquid agitation are designed for high speed rotation movements that cause movements of the whole volume. During very slow rotation, the volume and the dimensional range moved by these agitators are very limited therefore can not reach good agitation effects. It is desirable to have a specially designed liquid agitator that can reach better agitation effects from slow speed rotation, especially for the concaved or conical volume in which the height gradually decreases from the middle point to the side wall point.

One of the methods to heat greenhouse is to use a rocket stove by burying its chimney tube in ground to hold heat from the circulating combustion flue gas. This is a right way to "degrade" by burning large branches and tree trunks which cannot be acceptable to the onsite composters. But this method causes exhaust gas emission because the combustion flue gas goes directly into the atmosphere.

Studies have proved that plant growth can be stimulated by elevation of CO2 ppm [HortScience Vol 46(2):158-162 February 2011]. This method has been practiced in greenhouse farming. Studies have also proved that high concentration (up to 10,000 ppm) of CO2 can kill pests inside a closed space, therefore CO2 has been used as fumigant for stored grain utility (Nathan J Dyrud: University of Minnesota Extension Service (2001), Private stored grain fumigation manual 3-3).

In recycling the bio-degradable wastes into good staff for growing uses, the prior arts tend to deal the processes separately therefore don't solve the problem in high efficiency and even cause problems to each other. The apparatuses designed to treat solid wastes take the leachate liquid and exhaust gases as extra burdens which have to be specially managed. The apparatuses designed to treat waste waters take the solids inside as extra burdens which have to be specially managed. The apparatuses designed to treat exhaust gases have to employ liquid and solid filter media. The apparatuses designed to produce compost tea have to create conditions to grow microorganisms from the completed compost in which most of the microorganisms are not in the best state of activity and quantity. The apparatuses designed for vermi-composting have to manage the humidity of the fed solid waste, and the fed waste has to undergo a first stage of composting before it becomes food for worms. In winter, we need to buy fire woods or gas to heat a greenhouse while we put a lot of staff that is good for heating by burning into garbage bins that causes a lot afterward works to have it treated somewhere far away.

In the patent application US 2007/0059819A1, Stephen Storch discloses an apparatus for brewing compost tea composing of a plurality airlift pumps for agitation and aeration. This design causes a swirling vortex in the tank. Most of the nowadays apparatuses used for brewing compost tea have employed this technique, however, in all the apparatuses the swirling vortex is created for agitation and aeration only, the kinetic energy of the swirling vortex is not harnessed for good use.

It is desirable to have a system that integrates together all the functions of the above mentioned prior art apparatuses in which every burden becomes a good input into a circulating process. It is further desirable that the kinetic energy from the swirling vortex can be harnessed for good uses in an integrated system such as mixing and agitating solid wastes.

It is also desirable to have a specially designed turbine that can harness the kinetic energy from the swirling vortex in high efficiency.

SUMMARY OF THE INVENTION

The present invention is a composting bioreactor system that can continually receive biodegradable solid wastes, waste waters and exhaust gases, automatically recycle the biodegradable wastes into nutrients and heat energy, and automatically supply the nutrients and heat into an integrated hydroponic or aquaponic system. The invention together with the integrated food growing system can be installed onsite in places such as household balconies, household backyards and premises of restaurants and food factories etc. It can lead to zero mileage targets both for recycling the wastes and for growing the foods consumed in the same location. It can fully recover and reuse all the nutrients and heat energy from the treated wastes. It can also reach the target of nearly zero pollution to the environment during all processes. For better operational efficiency, an oblique cone agitator, a chisel plow agitator and a vortex flower turbine are specially designed for the bioreactor system.

The present invention comprises a bioreactor body, an extension, a central control unit and a stove unit. The bioreactor body is an insulated and sealed vessel with two (upper and lower) separators to divide the inside volume into three chambers (the upper chamber, the middle chamber and the lower chamber). It has a mixing agitation module, an aeration module and a heating module installed. Preferably, the aeration module composes a plurality of airlift pumps so that a swirling vortex in the middle chamber is created. The bioreactor body has inlets including waste water inlet(s) and exhaust gas inlet(s) and outlets including liquid outlet(s) and air outlet(s). A feed module on the top lid is cylindrical or other shapes of cross-section. The feed module has a door on each end and the two doors can be interlocked and controlled by an infrared auto-sensor on the top end. Sensors for temperature, humidity, oxygen, ammonia, carbon dioxide and air pressure are installed inside the bioreactor body vessel and connected into the central control unit. The mixing agitation module has a motor installed on the top lid to drive a shaft rod installed through the top lid by way of a bearing, and there fixed on the shaft rod are agitation mechanisms inside the upper chamber and the middle chamber of the body vessel.

The extension of the bioreactor system stays inside a wicking bed and works as its water reservoir. It composes an upper channel, a middle channel and a lower channel as well as a plurality of wick posts on the top wall. When the stove unit is employed it has a heat radiator staying under the bioreactor body vessel and works as its support base.

This invention integrates the composting process with the aquaponic technology together therefore upgrades aquaponics into compoponics, a specially created word to epitomize specifications and functions of the integrated system. A compoponic system, composing of this invention with soil wicking growing beds, an aquaponic system with soilless hydroponic growing beds, a wetland growing bed, an activated carbon growing bed and a greenhouse, mimics nature in a wider range than aquaponics in establishing both a closed-loop recirculation of water and gases, and a recirculation of nutrients, carbon and energy among human being, animals, microorganisms and plants by way of photosynthesis, slow burning by cellular respiration and burning by combustion.

Other objects, features, and advantages of the present invention will be readily appreciated from the following description. The description makes reference to the accompanying drawings, which are provided for illustration of the preferred embodiment. However, such embodiments do not represent the full scope of the invention.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF THE DRAWINGS

Figure 1:
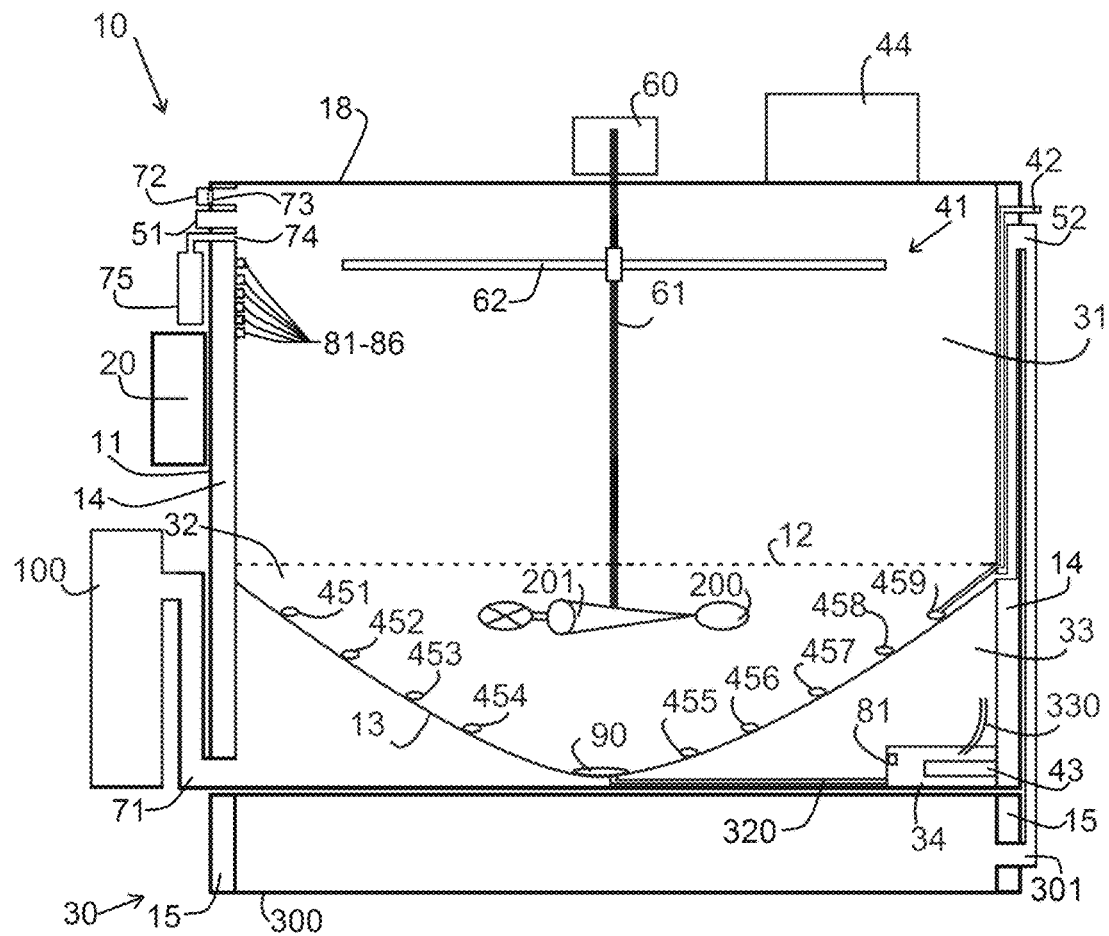
FIG. 1 shows a bioreactor body configured with an aeration module comprising perforated pipes and with a mixing agitation module driven by a motor.

As shown in FIG. 1, a composting bioreactor system of the present invention comprises of a bioreactor body 10, an extension 100, a central control unit 20 and a stove unit 30. The bioreactor body 10 has an insulated and sealed vessel 11 with two (upper and lower) separators 12-13 to divide the inside volume of the body vessel 11 into three chambers—the upper chamber 31, the middle chamber 32 and the lower chamber 33. The bioreactor body 10 also has a mixing agitation module 41, an aeration module 42 and a heating module 43 installed inside the body vessel 11 of which its side walls has an insulation layer 14. The bioreactor body 10 has several inlet ports, including waste water inlet(s) 51 and exhaust gas inlet(s) 52 and outlet ports, including liquid outlet(s) 71 and air outlet(s) 72.

Figure 2A:
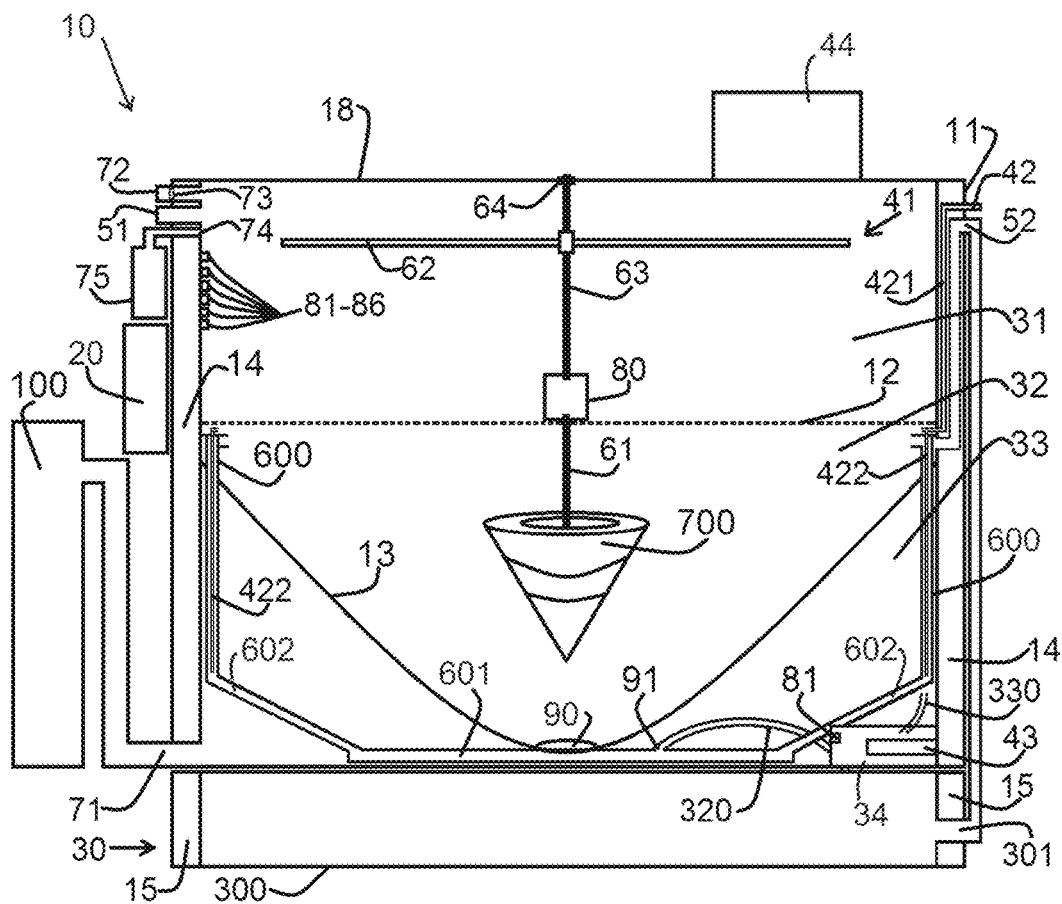
FIG. 2A shows a bioreactor body configured with an aeration module comprising airlift pumps and with a mixing agitation module driven by a vortex flower turbine with a coaxial gear reducer installed above the upper separator.
Figure 2B:
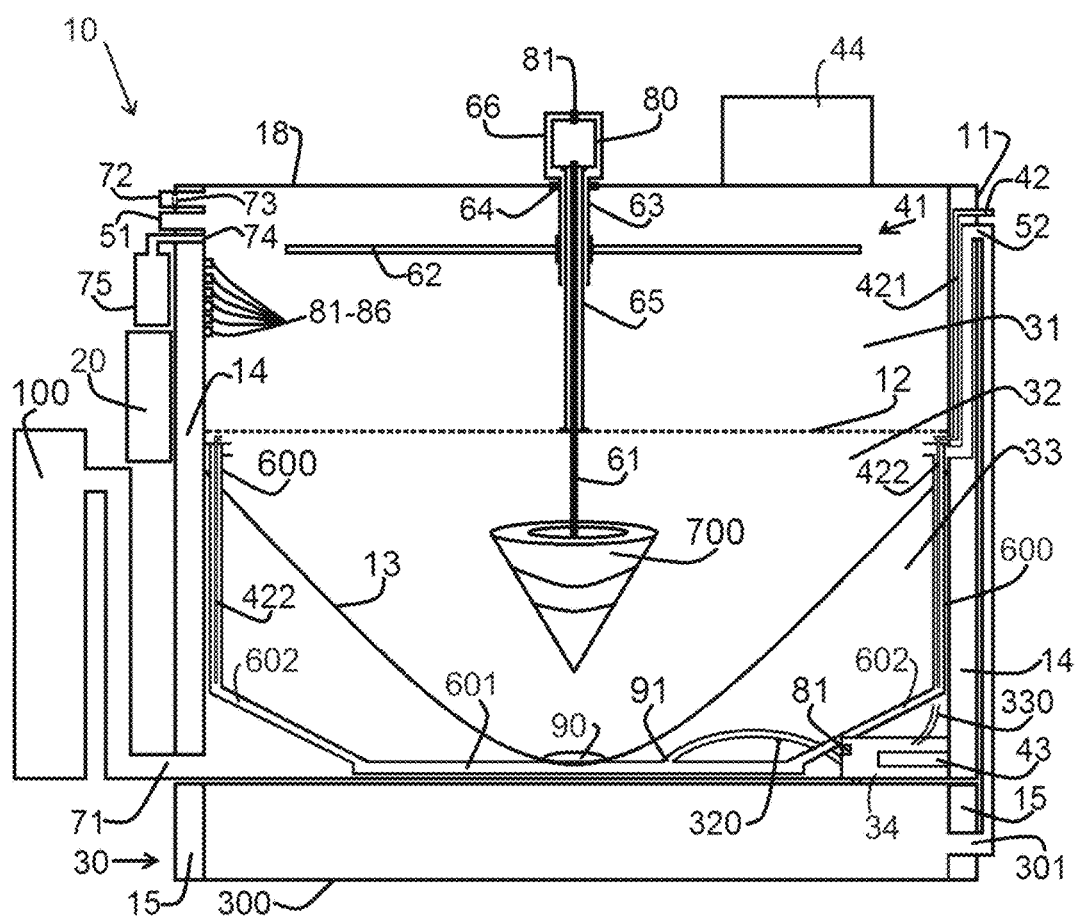
FIG. 2B shows a bioreactor body configured with an aeration module comprising airlift pumps and with a mixing agitation module driven by a vortex flower turbine with a coaxial gear reducer installed above the top lid and having two alongside coaxial shaft rods.
Figure 3:
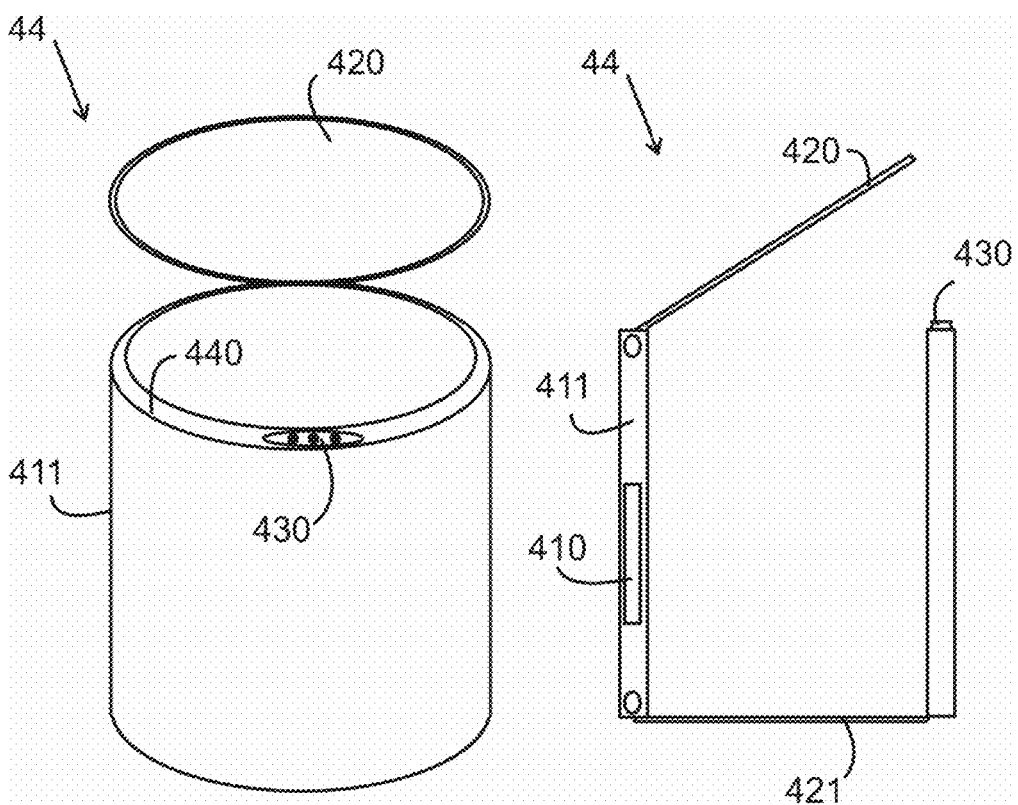
FIG. 3 shows perspective and cross section of a feed module.

As shown in FIGS. 1-3, the bioreactor body 10 has a feed module 44 on the top lid 18 of the body vessel 11. The feed module 44 is preferably a cylindrical feed port, however, it can have any other cross-sectional shape, such as rectangle or square. The feed module 44 has a control circuit 410 inside its side wall 411 and motorized doors 420, 421 on each end. The doors 420, 421 are interlocked and controlled by an infrared auto-sensor 430 on the top end 440. Preferably, at least the bottom door 421 or both doors 420-421 are slide doors or tubular rolling doors, which can be engaged with its slide-way edges to maintain good sealed state when pushed by air pressure from inside the body vessel 11. When the infrared auto-sensor 430 detects thermal human movements the top door automatically opens to allow feeding of wastes. The top door 420 stays open as long as there is a thermal human movement. Once the human movement is not detected for a certain time (for example 2 seconds), the top door 420 automatically closes. Then, the bottom door 421 automatically opens after certain time (for example 3 seconds) to allow the waste inside the feed module 44 to drop into the upper chamber 31 of the body vessel 11. The bottom door 421 automatically closes after certain time (for example 3 seconds) after it opens and if the top door 420 is closed. The system may also be configured to let the bottom door 421 automatically open if the top door 420 is stayed open for a certain time (for example 5 seconds). This allows continuous feeding of wastes including waste water into the upper chamber 31. In this case, the bottom door 421 closes at a certain time (for example 3 seconds) after the top door 420 is closed. This function may also be realized by having a specially designed push button on the side wall 411 of the feed module 44 and/or on the central control unit 20. Preferably, the control circuit 410 may be connected into the central control unit 20 to control and monitor the opening and closing of each door from the central control unit 20.

A plurality of sensors 81-86 for monitoring temperature 81, humidity 82, oxygen 83, ammonia 84, carbon dioxide 85 and air pressure 86 are installed inside the body vessel 11 and are connected into the central control unit 20.

The mixing agitation module 41 has a motor 60 installed on the top lid 18 to drive a shaft rod 61 installed through the top lid 18 by way of a bearing. Fixed on the shaft rod 61 are an agitation mechanism 62 inside the upper chamber 31 and an agitation mechanism 200 inside the middle chamber 32 of the body vessel 11.

The upper separator 12 is a substantially flat perforated board to separate particles with diameters larger than certain size (for example ½-¼ inch). Therefore, the upper separator filters relatively large particles.

The lower separator 13 is a concaved dish or a conical separator, which has a drain 90 at its center (middle lowest part). The liquid from the middle chamber 32 drains into a heating sub-chamber 34, which is located in the lower chamber 33. There is a filter on the top of the drain 90 to separate particles with diameters larger than a certain size (for example ¼-⅛ inch). Clearly, this filter separates smaller particles than that of the upper separator 12. The lower separator 13 is made of thermal conductive material so that the liquid inside the middle chamber 32 exchanges heat with the liquid in the lower chamber 33.

The middle chamber 32 is equipped with an aeration module 42. The aeration module comprises of a series of air pipes 451-459 positioned in circular manner on the upper surface of the lower separator 13. The air pipes are perforated to introduce air into the middle chamber 32, thus aerating the waste materials both inside the middle chamber 32 and the upper chamber 31.

The liquid collected in the lower chamber 33 exits the body vessel 11 from the liquid outlet port 71. Since the drain 90 is in the middle lowest part of the lower separator 13, it is easy to remove most of the liquid inside body vessel 11 through the liquid outlet 71, especially when the body vessel 11 is moved from one spot to a new spot.

Figure 4A:
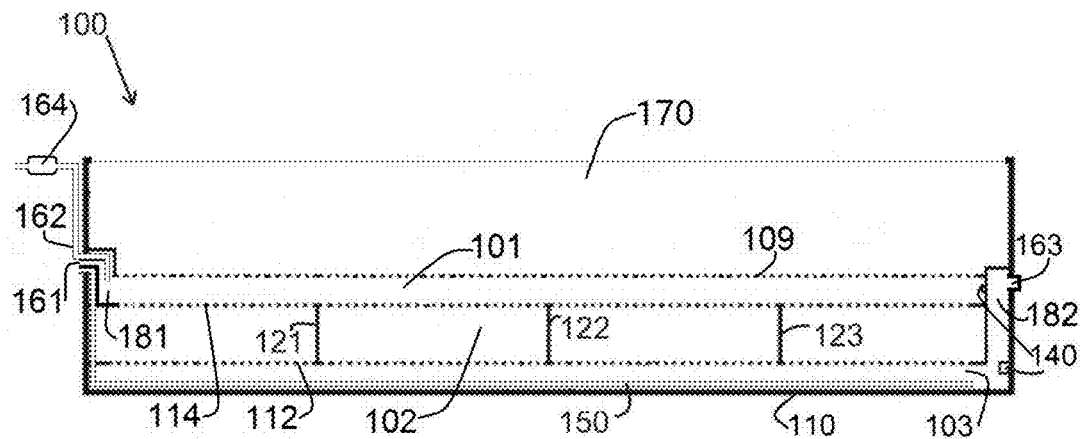
FIG. 4A shows a sectional elevation and a cross-sectional elevation of an extension without wick posts on the top wall.
Figure 4A:
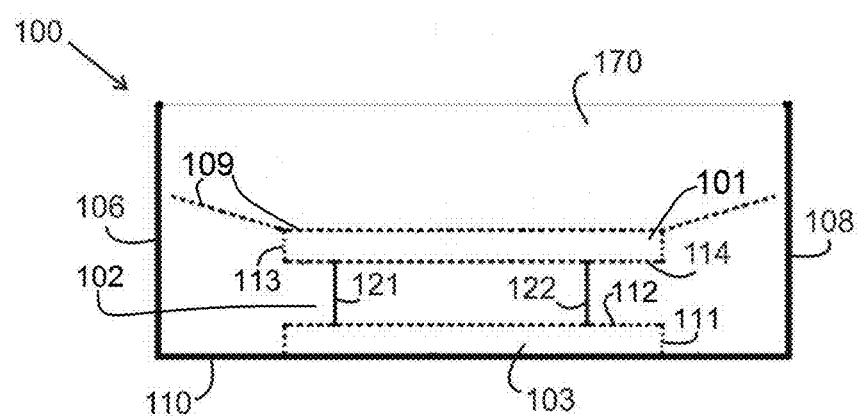
Figure 4B:
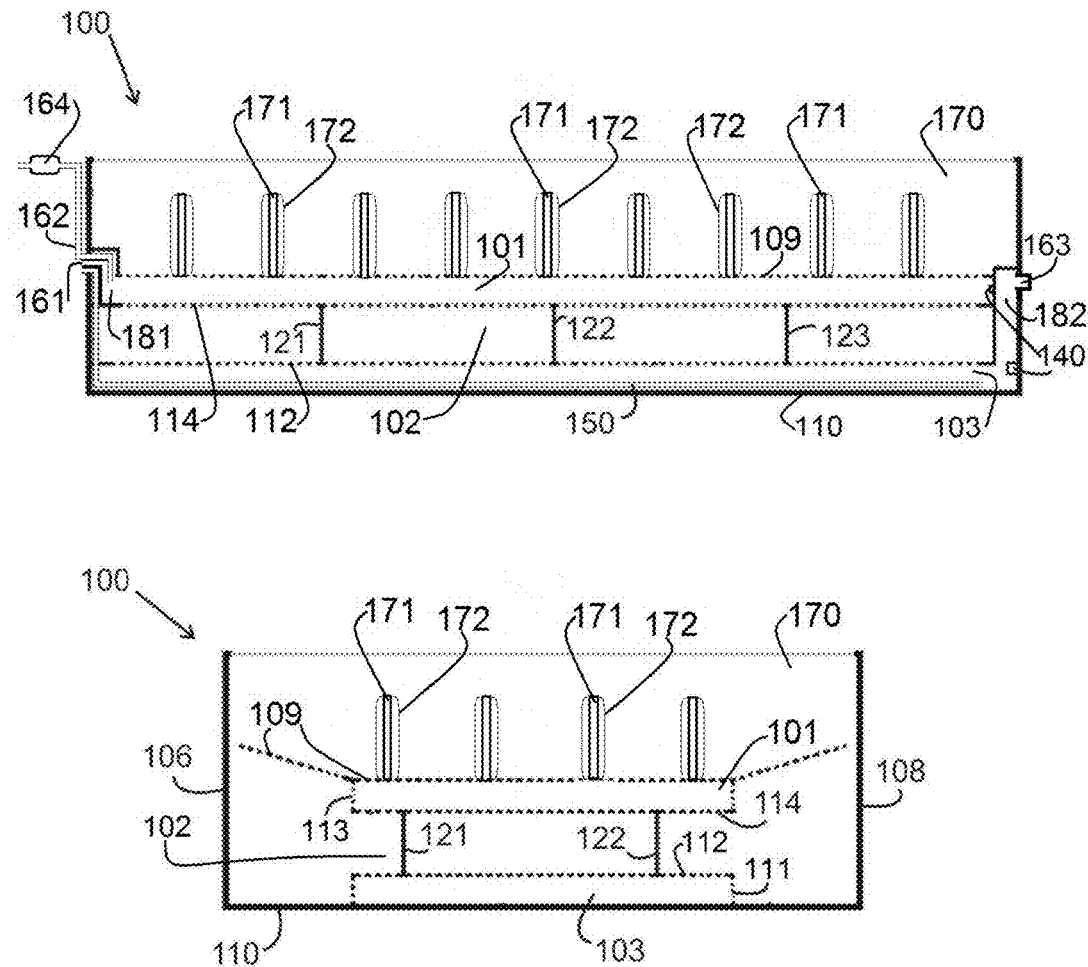
FIG. 4B shows a sectional elevation and a cross-sectional elevation of an extension with wick posts on the top wall.

The lower chamber 33 has a heating-sub-chamber 34. This sub-chamber 34 has a relatively small size (e.g., smaller than 6×6×12 inches) so that it can maintain a high temperature using a small electric heater. The heating-sub-chamber 34 is preferably installed on the bottom wall of the body vessel 11 and its top and side walls are insulated to prevent heat losses. The liquid exiting the middle chamber 32 through the drain 90 enters the heating-sub-chamber 34 by way of the inlet pipe 320. Heated liquid leaves the heating-sub-chamber 34 from an outlet pipe 330 to enter inside the remaining volume of the lower chamber 33. The inlet 320 and outlet 330 pipes for the heating-sub-chamber 34 are small-sized (for example with cross-sectional diameter smaller than 3 inches) and have a length of at least ⅓ of the diameter of the vessel bottom wall so that its inside volume is relatively separated from the middle chamber 32 and from remaining volume of the lower chamber 33. The heating module 43 is installed from outside of the side wall of the body vessel 11 into the heating sub-chamber 34. Temperature inside the heating sub-chamber reaches 70-100° C. (much higher on the electric heater surface of heating module 43) to kill pathogen microbes and weed seeds etc. of the liquid stream flowing through the heating-sub-chamber 34. The liquid in the remaining volume of the lower chamber 33 moderates the high temperature liquid from the heating-sub-chamber 34 therefore the liquid introduced into the extension 100 through the liquid outlet 71 is in a temperature range that is good for plants and worms growing in the wicking bed 170 above the extension 100 as shown in FIGS. 4A-B.

When the stove unit 30 is employed, it is mostly used when the ambient temperature is low. All the volume inside the lower chamber 33 is heated by the stove radiator 300 therefore the heating module 43 runs less. The heat from stove radiator 300 reaches to all contents of the body vessel 11 therefore help maintaining a good condition for the composting process. The heat from stove radiator 300 also reaches into the extension 100 and the integrated growing beds by water circulation from the lower chamber 33 of the body vessel 11 into the extension 100 and then into the integrated growing beds.

The mixing agitation module 41 may employ any prior art motors and agitation mechanisms that fit for the bioreactor body 10. Preferably, the motor 60 is a slow speed motor (for example less than 10 rpm) so that it consumes less electricity, causes less noise and produces larger torque to rotate the agitation mechanisms 62 and 200.

Preferably, the agitation mechanism 200 inside the middle chamber 32 is composed of a plurality of cones 201 horizontally installed on balanced circle frames 202 so that it can cause more volume of liquid to move by slow rotation and increase the liquid travel distance by each rotation because of the height of the cone 201. Further preferably, it is composed of a plurality of oblique cones 201 made by method as shown in FIGS. 5A-F. It is easier to install the oblique cones 201 made by this method on a horizontally flat frame surface. When an oblique cone 201 is installed horizontally along its longest ht line the axis of the oblique cone is in a tilted angle (nearer to perpendicular) opposite to the upper surface of the concaved or conical lower separator 13, this angle helps the rotated volume of liquid pushing along the surface harder therefore producing more secondary liquid currents from the rotations.

The oblique cones 201 may be arranged with one or more installation combinations of different 3-dimensional space positions. As shown in FIGS. 5D-F, typically they are serially installed on a circle frame 202 with the line from apex point t to the longest slant height point h horizontally aligning with the lower surface of an arc chord of the circle frame with at least two points fixed. The longest slant height point h on the base is the most forward top point is therefore named head point of the oblique cone 201. A part near the apex point t of one oblique cone 201 can be arranged inside the part near to the head point h of another neighbored oblique cone 201 so that more oblique cones 201 can be installed on one circle frame 202. One agitator can employ a plurality of circle frames 202 which are horizontally arranged or vertically arranged. When the circle frames 202 are vertically arranged, the diameter of the lower circle frame 202 is smaller than the diameter of the upper circle frame 202 so that the agitator works well above the concaved or conical lower separator 13. When more than one circle frames 202 are employed, the size of oblique cones 201 maybe specially configured for each of the circle frames 202. All oblique cones 201 installed on one agitator are all in the same clockwise or anti-clockwise direction, the same as the rotation direction of the driven motor 60.

Figure 5A:
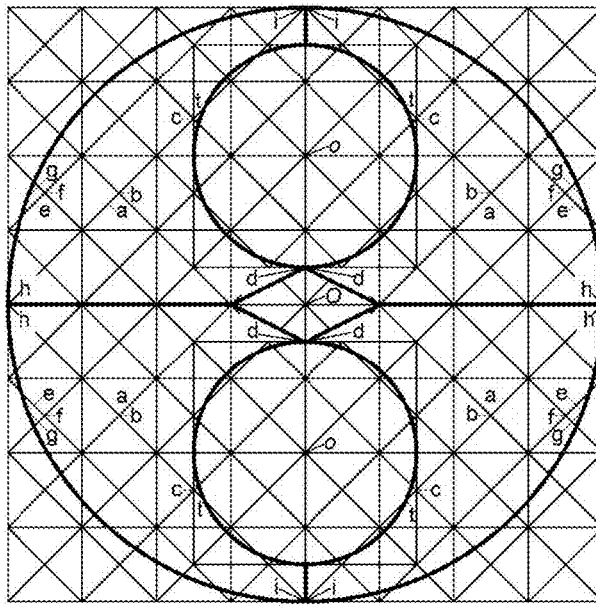
FIGS. 5A-C show geometry drawings and method for making a prototype sample of an oblique cone agitator.
Figure 5B:
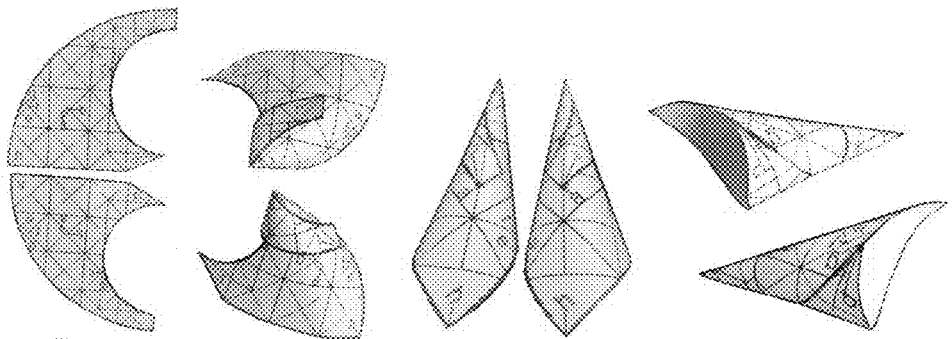

Details for making the oblique cones 201 are showing in FIGS. 5A-B.

(1) Inside of a circle O draw two equal circles o and a rhombus based on the given spaces and points.
(2) Find the intersection point t of the inner circle o and the line segment hi which has a part staying inside the inner circle o.
(3) Based on point t find the length of the line segment tc, and find point a and point e based on the length of tc, so that tc=ab=ef.
(4) Point g is a point on the circle O which is perpendicular to of at point e.
(5) Harvest the 4 pieces of blades by cutting the thicker lines.
(6) Fold the blade by turning it into opposite directions at the turning point t to form the shape of an oblique cone.
(7) Adjust the shape so that point i coincides with point a and point d coincides with point g.
(8) Point t is referred as apex point and point h is referred as the point which has the longest slant height of the oblique cone.
(9) The area along the line segment ht is relatively flat therefore is good for align with a flat surface of a frame.

When the oblique cone is installed on a circle frame and the line ht is in horizontal level, h is the most forward point therefore is named head point while t is the aftermost point therefore is named tail point. At this position axis of the oblique cone tends to be in an tilted angle near to perpendicular to the opposite concaved or conical surface of the lower separator 13.

The size of the circle frame 202 depends on both the quantity of oblique cones 201 to be installed and the length in arc chord of the circle for each cone to occupy on the circle. Since the tangent value of an known angle can be found from a tangent chart, the radius of a circle frame can be calculated according to the Pythagorean Theorem for a given quantity of oblique cones 201 to be installed and a given length in arc chord for each oblique cone to occupy on the circle frame 202.

Figure 5C:
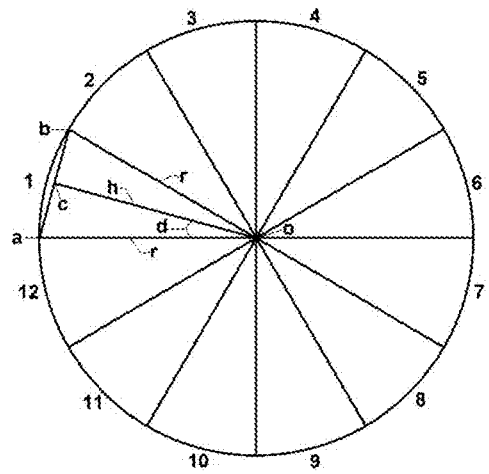
Figure 5D:
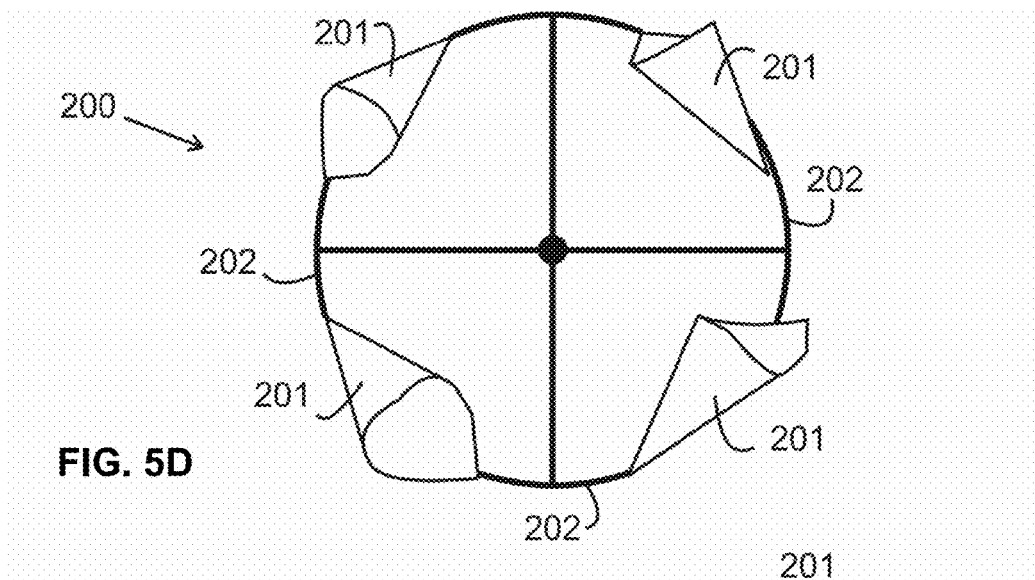
FIGS. 5D-F show method to install oblique cones on circle frames for making an prototype sample of an oblique cone agitator.
Figure 5E:
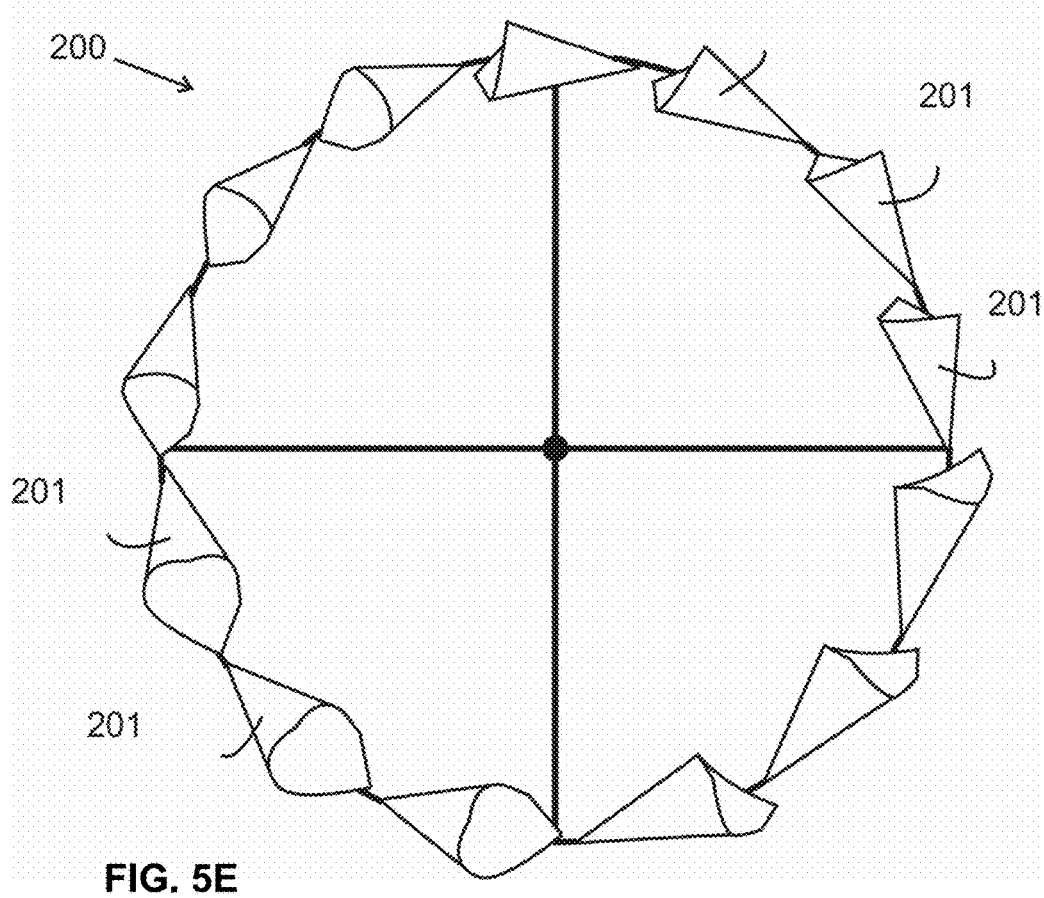
Figure 5F:
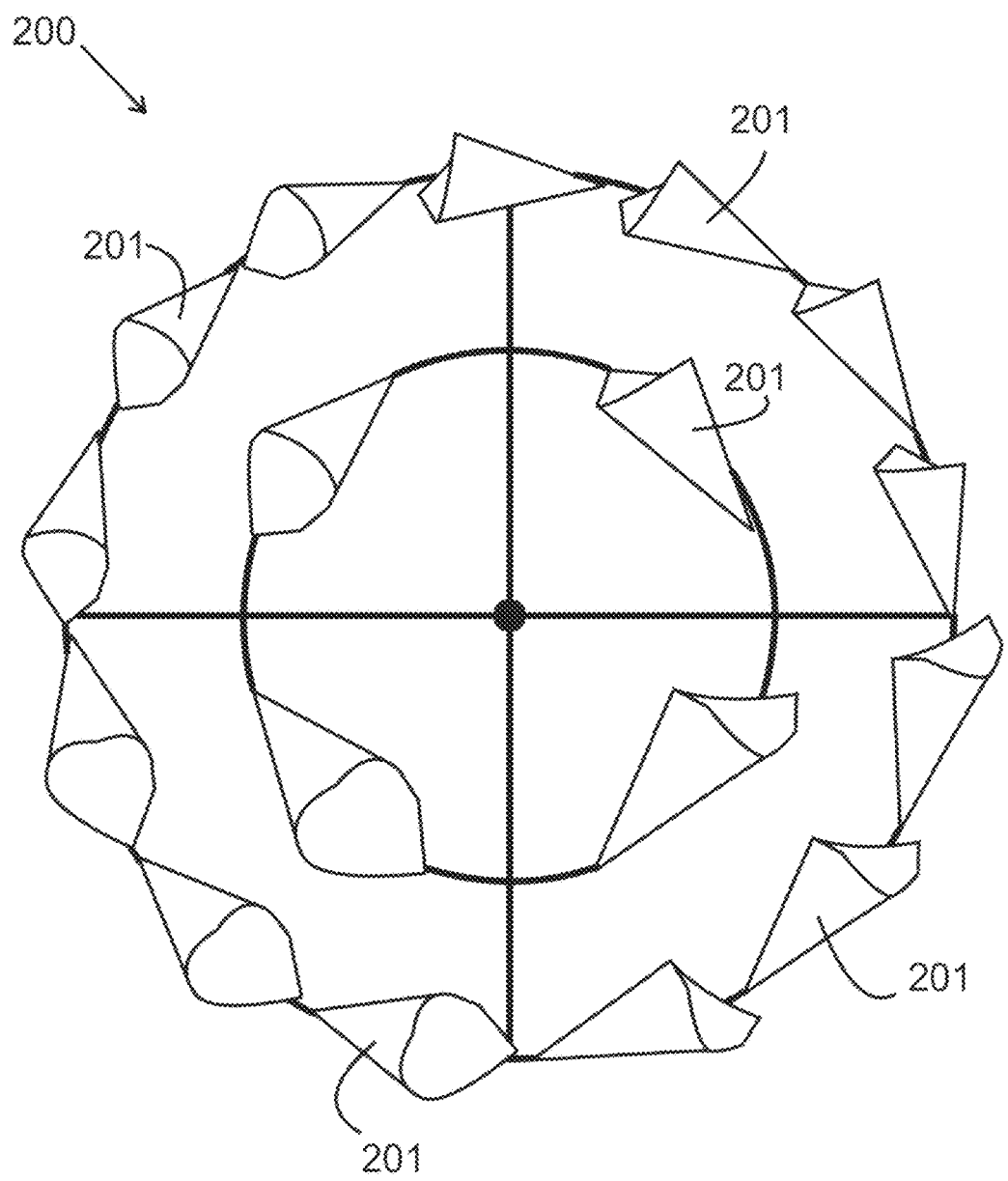

As shown in FIG. 5C:
If the length of arc chord ab is 10 cm and 12 oblique cones are to be installed,
Then: ac=10/2=5 cm
angle d=½(360/12)=15°
tan d=tan 15°=0.26795
Since: tan d=ac/h=5/h,
Then: h(tan d)=5
Therefore: h=5/(tan d)=5/0.26795=18.66
Since: $ac^2+h^2=r^2$,
Then: $r^2=ac^2+h^2=5^2+18.66^2=25+348.1956=373.1956$,
Therefore: r=square root of 373.1956=19.31827 cm.

Figure 5G:
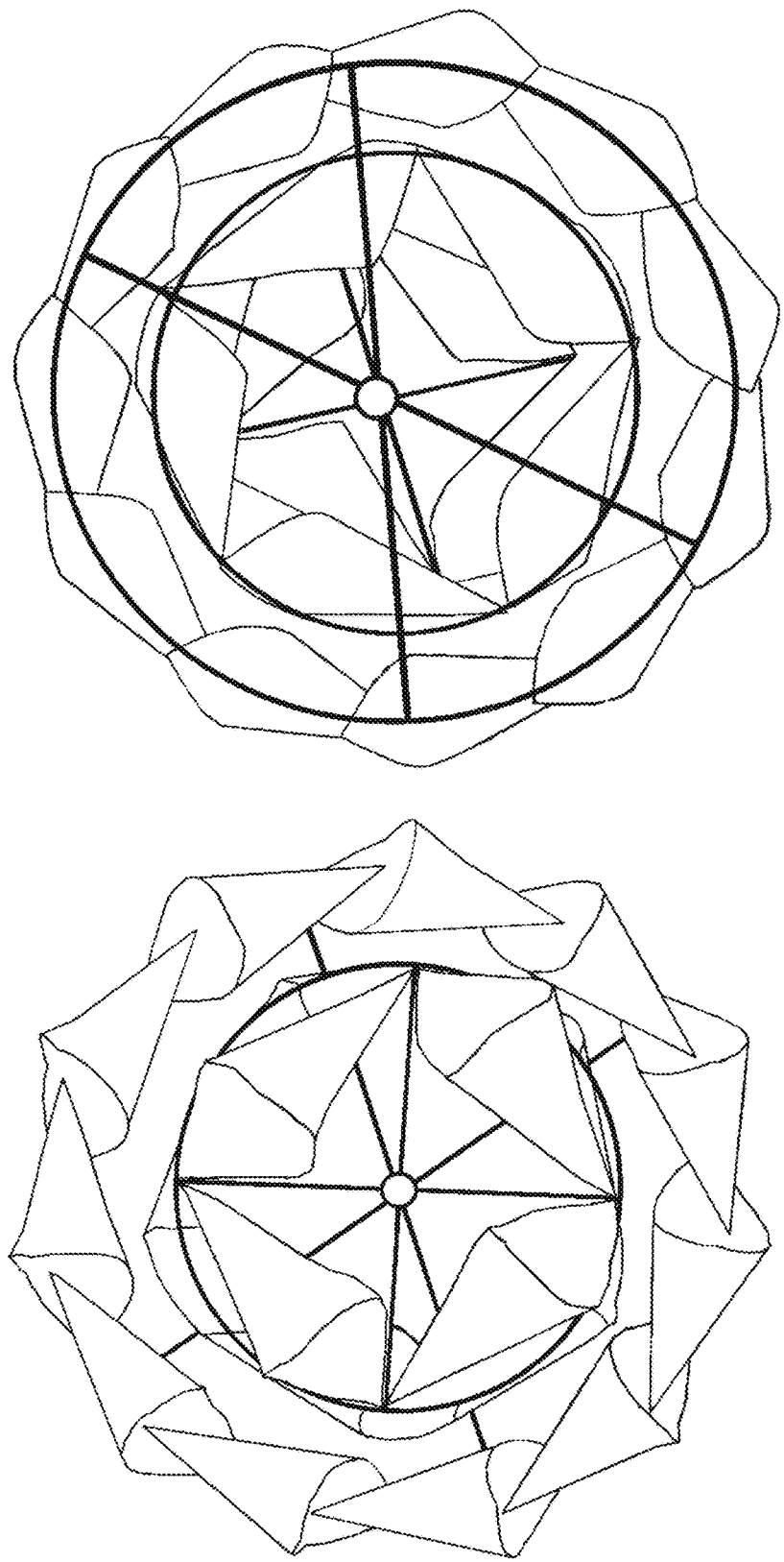
FIG. 5G shows a top view and a bottom view of a prototype sample of an oblique cone agitator comprising 20 oblique cones installed on 3 circle frames in 2 vertical layers.

FIGS. 5D-F shows the method of making prototype oblique cone agitator samples by installing oblique cones 201 on circle frames 202. FIG. 5G are drawings from pictures of both a top view and a bottom view of a prototype sample of the agitator that has 20 oblique cones installed on 3 circle frames vertically in two layers. The upper layer has two circle frames in the same horizontal level. On the upper outer circle frame 11 oblique cones are serially installed with some part near to the tail t point of the front oblique cone staying inside the part near to the head h point of the oblique cone immediately after. On the upper inner circle frame 5 oblique cones are serially installed with the tail t of the front cone right contact with the head h of the oblique cone immediately after. On the lower layer circle frame 4 oblique cones are installed of which the ht lines are perpendicular to each other for any two neighboring oblique cones. All the 16 oblique cones on the 2 upper circle frames are of the same size. The 4 oblique cones on the lower circle frame are of a larger size than the cones of the upper layer.

Figure 6:
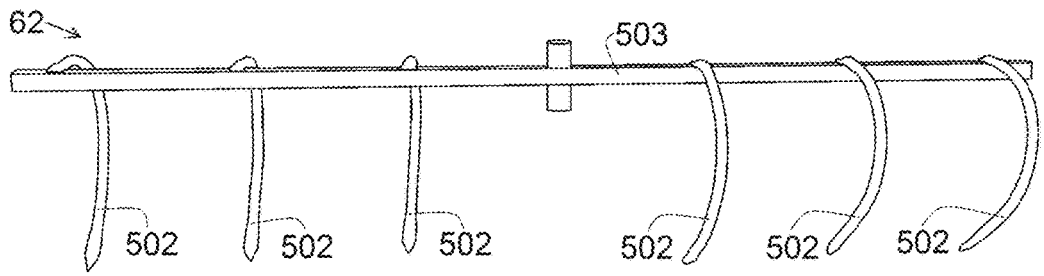
FIG. 6 shows a perspective view of a chisel plow agitator.

As show in FIG. 6, preferably, the agitation mechanism 62 inside the upper chamber 31 is a chisel plow agitator composed of a plurality of chisel plows 502 installed on a balanced horizontal frame 503. The frame 503 is staying vertically near to the top lid 18 so that the chisel plow agitator 62 meet with less resistant force during rotating inside the upper chamber 31. The vertical length of the chisel plows 502 fits to the height of the upper chamber 31 and tips of the chisel plows 502 reach to nearby of the upper separator 12. At least one pair of chisel plows 502 are in a position near to the side wall of the upper chamber 31 (for example in a position from the draft rod point of no less than ⅔ of the chamber horizontal radius) so that the content along the side wall is well agitated.

The second embodiment of the present invention is shown in FIGS. 2A-B. Preferably, the aeration module 42 comprises of a plurality of airlift pumps 600 so that a swirling vortex in the middle chamber 32 is created, and a specially designed vortex flower turbine 700 shown in FIGS. 7A-H is configured to harness the kinetic energy of the swirling vortex. In this configuration, the drain outlet 90 in the middle lowest area of the lower separator 13 is connected into the water pipes 601, 602 of the airlift pumps 600. An outlet 91 from the main water pipe 601 near to the drain 90 is created to introduce liquid into the heating-sub-chamber 34 by way of inlet pipe 320. The upper separator 12 is in a higher position so that there is enough volume in the middle chamber 32 to hold water for creating the swirling vortex. A plurality of airlift pumps 600 are installed from under the lower separator 13 and through to above the lower separator 13. The airlift pump pipes above the lower separator 13 are arranged in the same clockwise or anticlockwise angles so that an swirling vortex is created. Since the swirling vortex in the middle chamber 32 itself agitating the liquid very well, the agitation mechanism 200 of the mixing agitation module 41 inside the middle chamber 32 is therefore omitted.

One of the options to install the air pipes for the airlift pumps is to have a circle pipe with a plurality of T-connectors fixed on the lower surface of the upper separator 12. The air pipe from inlet pipe 421 of the aeration module 42 is connected with the circle pipe. The air pipe 422 for each of the airlift pump 600 is connected with a t-connector on the circle pipe and is installed into the airlift pump 600 for certain depth through the top of the airlift pump 600.

As shown in FIG. 2A, the mixing agitation module 41 is composed of a chisel plow agitator 62 in the upper chamber 31, a bearing 64 on the top lid 18 to hold a shaft rod 63 of the chisel plow agitator 62, a vortex flower turbine 700 in the middle chamber 32, and an opposite coaxial gear reducer 80 fixed on the upper surface of the upper separator 12 with its input shaft connected with the shaft rod 61 and its output shaft connected with the shaft rod 63. In this case, the swirling vortex causes rotation of the turbine 700 in the middle chamber 32 and then rotates the chisel plow agitator 62 in the upper chamber 31 in reduced speed and increased torque by the gear reducer 80. The motor 60 used to drive the mixing agitation module 41 is therefore omitted.

Preferably, as shown in FIG. 2B, the opposite coaxial gear reducer 80 may be installed above the top lid 18 so as to prevent the gear reducer 80 from erosion by the liquid inside middle chamber 32. The shaft rod 61 of the vortex flower turbine 700 is connected with the input shaft of the gear reducer 80. Outside the shaft rod 61 is a tube frame 65 with its lower end fixed on the upper separator 12 and its upper end fixed on the lower end of the gear reducer 80, to fix and support the gear reducer 80. Outside the tube frame 65 is a shaft rod 63 of the chisel plow agitator 62 held by a bearing 64 installed on the top lid 18. Outside the gear reducer 80 is a tube frame 66 of which the circle point part of its upper end is connected with the output shaft 81 of the gear reducer 80 and its lower end is connected with the shaft rod 63. In this case, the mixing agitation module 41 has two alongside coaxial shaft rods, the inner shaft rod 61 of the vortex flower turbine 700 and the outer shaft rod 63 of the chisel plow agitator 62.

The vortex flower turbine 700 is so named because it looks like a flower and both the flower leaf blades 701 and the channels between the flower leaf blades 701 are of the vortex feature. When the vortex flower turbine 700 is in rotation, swirling of the channels between the flower leaf blades 701 are almost in the same way of the swirling of a vortex current. When the vortex flower turbine 700 is engaged with a swirling vortex current, each of its rotation movement accelerates the swirling current therefore the counterforce and the drag produced are little.

As shown in FIGS. 7B-F, the vortex flower turbine 700 composes of a shaft rod 61 and a plurality of specially drawing leaf blades 701 that are folded around the shaft rod 61 into the vortex flower shape. The narrow ends of the leaf blades 701 are directly fixed on the lower end of the shaft rod 61 while the wide ends are fixed on the shaft rod 61 by way of diameter and circle frames 702. All the leaf blades 701 are properly adjusted so that they are in taut state and the width of the channels are much bigger along the top blade edges than along the bottom blade edges.

Figure 7A:
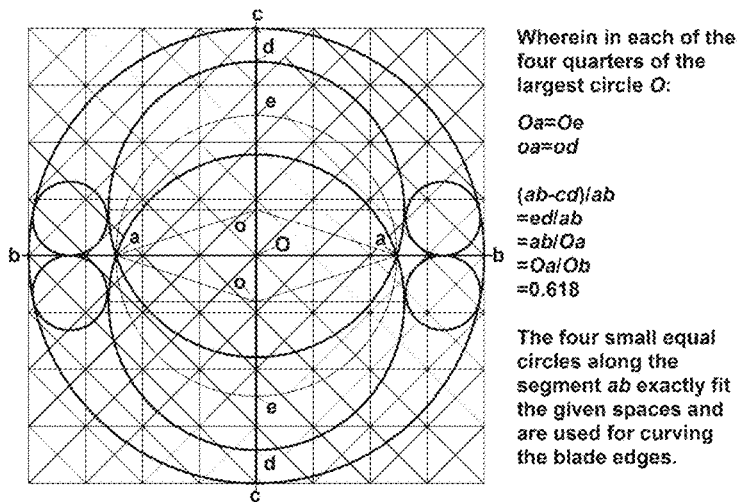
FIG. 7A shows geometry drawings for harvesting 4 leaf blades from a sheet to make a prototype sample of a vortex flower turbine.
Figure 7A:
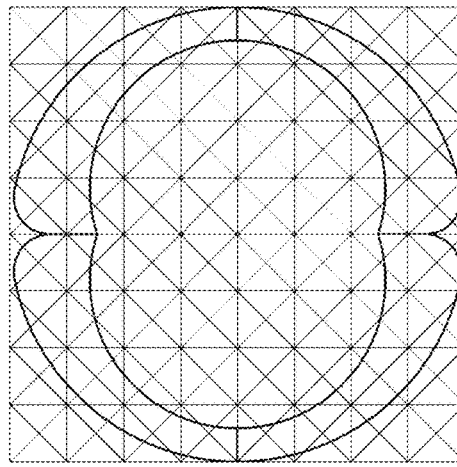

FIG. 7A shows geometry drawings to harvest 4 leaf blades 701 from a sheet. Point a divides the radius Ob into a golden ratio. Point d is so decided that (ab−cd)/ab=0.618. The circle point of the circle o passing points a and d is on segment Oc. The 4 little circles above and below the segments ab are equal and fit the given space exactly. They are used for curving the blade edges. Four leaf blades 701 are harvested by cutting the thicker lines of the drawing in FIG. 7A.

Figure 7B:
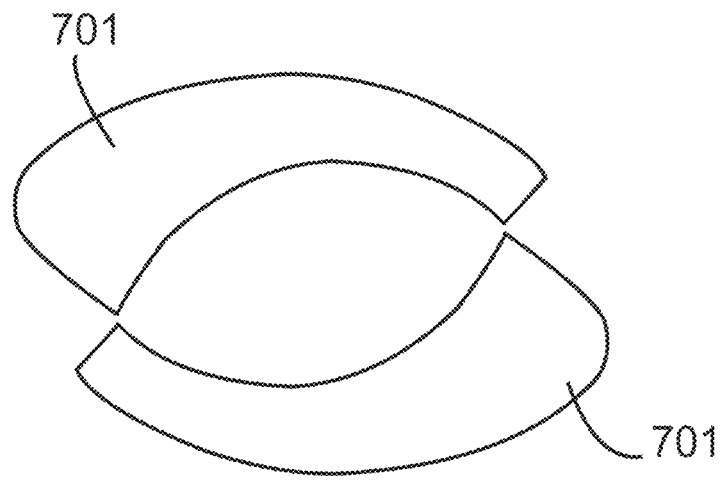
FIGS. 7B-D show method to make a prototype sample of a vortex flower turbine made of 2 leaf blades.
Figure 7C:
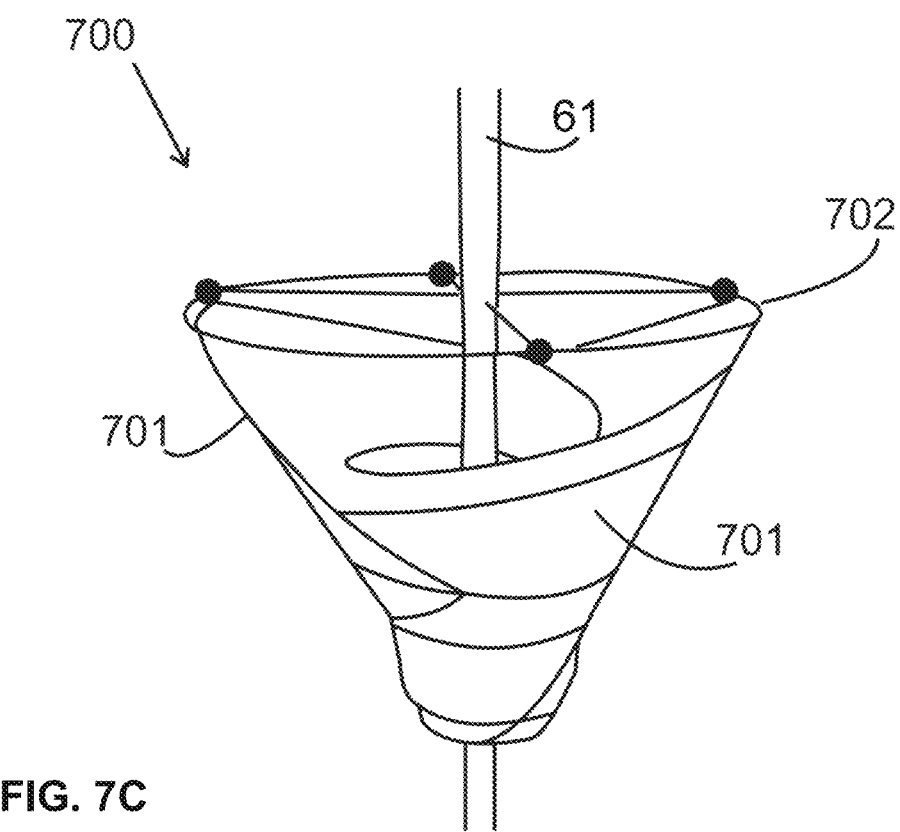
Figure 7D:
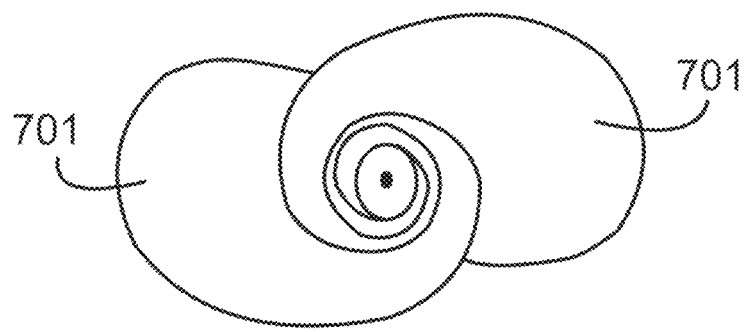
Figure 7E:
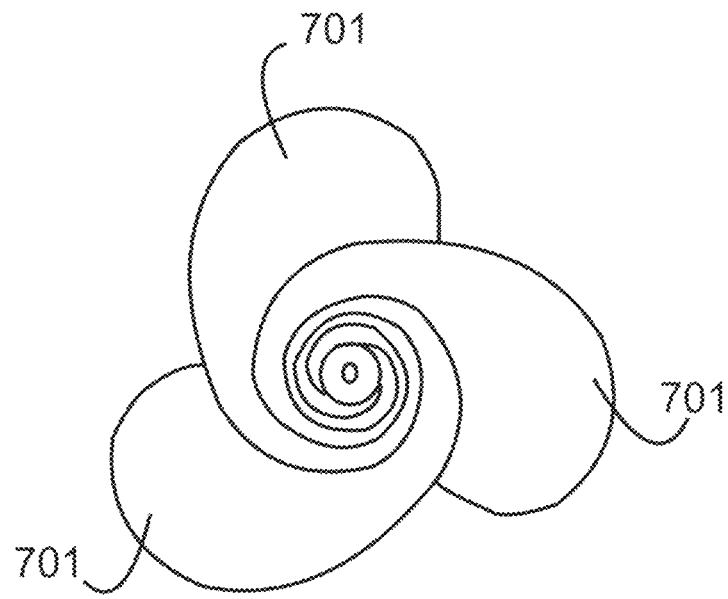
FIG. 7E shows a top view of a prototype sample of a vortex flower turbine made of 3 leaf blades.
Figure 7F:
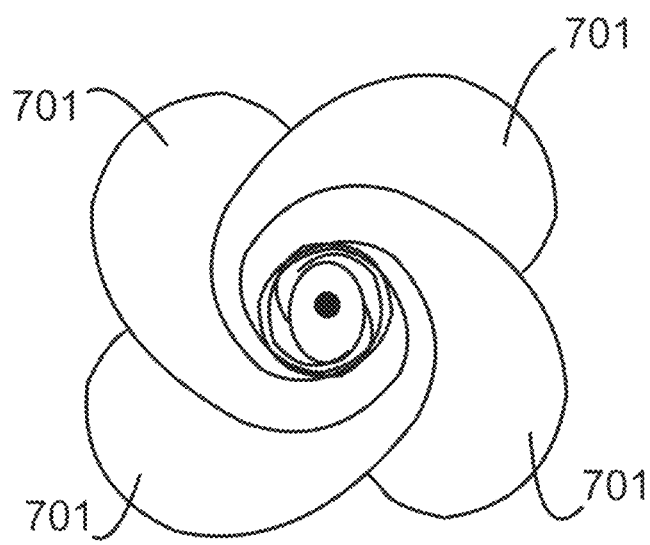
FIG. 7F shows a top view of a prototype sample of a vortex flower turbine made of 4 leaf blades.

FIGS. 7B-D shows the method for making a vortex flower turbine 700 by use of 2 leaf blades 701. FIGS. 7E-F show prototype samples of the vortex flower turbine 700 made either by use of 3 leaf blades 701 or 4 leaf blades 701.

Figure 7G:
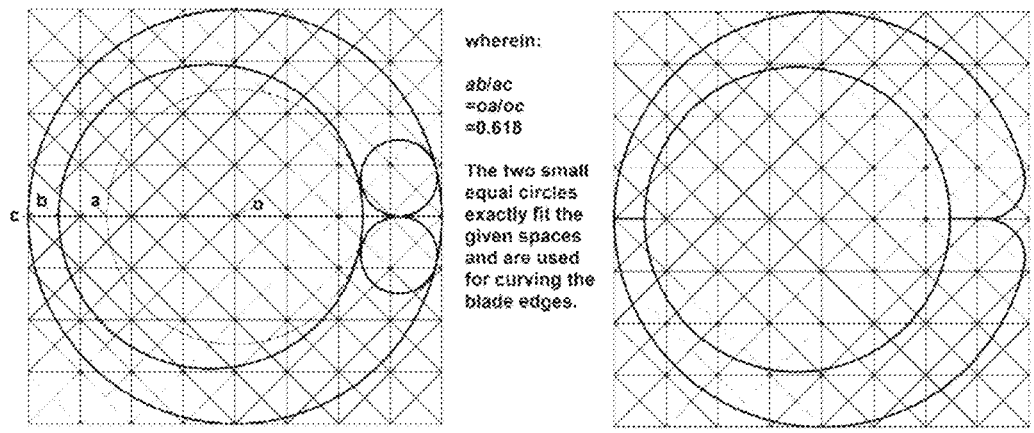
FIG. 7G shows geometry drawings for harvesting 2 leaf blades from a sheet for making a prototype vortex flower turbine.

As shown in FIG. 7G, optionally, another method to make the vortex flower leaf blades is to harvest 2 blades from one sheet. In FIG. 7G, point a is the golden ratio point of radius oc and point b is the golden ratio point of line segment ac wherein ab/ac=oa/oc=0.618. The circle points of the 3 circles passing points a, b and c are all on segment oc. The two small equal circles exactly fit the given space and are used for curving the blade edges. Since the leaf blades made in this optional method is longer, the vortex flower turbine made by these blades has longer swirl channels between the leaf blades therefore is better in accelerating the swirling current when engaged.

Figure 7H:
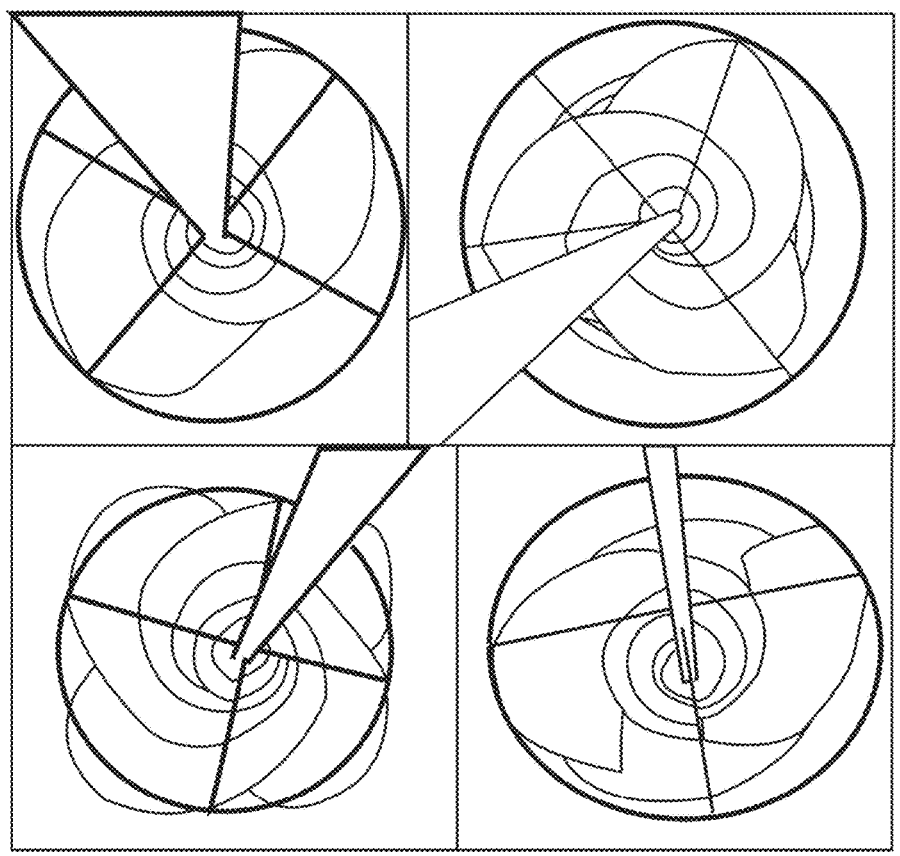
FIG. 7H shows top view of 4 prototype samples of the vortex flower turbine.

FIG. 7H shows the top view of 4 prototype samples of the vortex flower turbine 700.

The body vessel 11 can be any kind of shape of cross-section, preferably it is a cylinder. The height position of the lower separator 13 is so decided that all the components inside the lower chamber 33 can be easily installed. The height position of the upper separator 12 depends on the proportion between solid wastes and waste waters to be treated. The height position of the upper separator 12 is also related to the liquid height position introducing into the extension 100 from the liquid outlet 71. Preferably, when it is configured with the perforated air pipe aeration module 42 as shown in FIG. 1 the upper separator 12 is positioned below the middle point of height of the side wall of the body vessel 11 so that the upper chamber 31 has larger volume to hold solid wastes. Preferably, when it is configured with the airlift pump aeration module 42 as shown in FIGS. 2A-B the upper separator 12 is positioned higher so that the middle chamber has a larger volume to hold liquid for creation of a swirling vortex.

The air outlet 72, the inlet port of aeration module 42, the waste water inlet 51 and the exhaust gas inlet 52 are positioned on side wall of the upper chamber 31 near to the top lid 18, so that the inside liquid doesn't reflux to the pipes outside the body vessel 11. The inside pipe connected with the exhaust gas inlet 52 is turned down and pass through the upper separator 12 to reach inside the middle chamber 32.

Preferably, as shown in FIG. 1 and FIGS. 2A-B, the inlet port of aeration module 42 and the exhaust gas inlet 52 may be positioned on the side wall of the middle chamber 32. In this case, air pipes connecting with the inlet port of aeration module 42 and the exhaust gas inlet 52 outside the body vessel 11 stay inside the insulation layer 14 of the body vessel 11 and are turned up along outside of the side wall of the upper chamber 31 near to the top lid 18, to prevent liquid refluxing into the outside pipes. With this installation option, agitation operation inside the upper chamber 31 becomes easier because its side wall doesn't have resistance from the pipes.

Preferably, worms such as *Eisenia fetida* and flies such as *Hermetia illucens* may be cultured in the upper chamber 31, so that they help speed up the decomposition of the solid wastes inside the upper chamber 31 in which foods are available while conditions are good for worms and flies to grow. As shown in FIG. 1 and FIGS. 2A-B, preferably a collection container 75 may be connected with an output port 74 of the bioreactor body 10, so that the fly larvae escaped from the upper chamber 31 are automatically harvested to feed the aquaculture animals of an integrated aquaponic system.

Optionally, a part of the side wall of the upper chamber 31 may be a sealed gate or an openable mechanism so that the upper chamber 31 can be accessible from outside, in case it is required to remove the residue humus that is unbreakable. Also, a portion of the top lid 18 or the side wall of the body vessel 11 may be transparent so that the inside space can be seen and monitored from outside. The unbreakable residue humus removed from upper chamber 31 may be fed into the stove unit 30 to be further degraded by burning.

As shown in FIGS. 4A-B, the extension 100 comprises of three channels that are the upper channel 101, the middle channel 102 and the lower channel 103. Preferably, the middle channel 102 extends up and down along the side walls 106, 108, so that it reaches to the bottom wall 110 and the top wall 109. The parts of the top wall 109 near to the side walls 106, 108 are of open style so that bio-filter media such as lightweight expanded clay aggregate (LECA) or other medias can be loaded into the middle channel 102. The top wall 109 and the separator boards 111-114 between the channels 101-103 are all perforated to allow liquid to filter through. Preferably the extension 100 shares with the wicking bed for the side walls 106, 108 and the bottom wall 110 and some vertical support frames 121-123 are added between the separator boards 112 and 114. At least one temperature sensor 140 is installed in each of the upper channel 101 and the lower channel 103 and is connected into the central control unit 20. An aeration module 150 is installed inside the lower channel 103. Both the liquid outlet 71 and the air outlet 72 from the bioreactor body 10 are introduced into the chamber of the upper channel 101 by way of the liquid inlet 161 and air inlet 162.

At the extension end near to the bioreactor body 10, a chamber 181 is separated so that it can only connect into the upper channel 101. At the extension end far from the bioreactor body 10, a chamber 182 is separated so that it can only connect into the lower channel 103. In the chamber 182 of the far end, there is either an outlet 163 in the level of the upper channel 101 or a syphon to let go the liquid from the extension 100. When the syphon is employed, the syphon off level to stop liquid flowing out is set near to the bottom of the lower channel 103. Since air goes into inside of the channels during the liquid flowing out from the syphon, the aeration module 150 in the lower channel 103 is therefore omitted.

The extension 100 is to stay inside at the lower layer of a wicking bed 170 and to work as the water reservoir of the wicking bed 170. Top soil or compost or other media of 8-12 inches of thickness or other thicknesses is added in the wicking bed 170. Worms such as *Eisenia fetida* or other species are cultured in the wicking bed 170. The extension 100 supplies water, oxygen, nutrients, microorganisms and heat from lower layer to top layer of the wicking bed to grow worms and food plants. The worms are harvested for feeding the aquaculture animals of the integrated aquaponic system. As shown in FIG. 4B, preferably a plurality of wick posts 171 are installed on the top wall 109 of the extension 100 so that growing medias such as limestone gravel or crashed lava rock that are good to filter and to degrade exhaust gases but not good in wicking can be employed for the top layer of the wicking bed 170. Wicks 172 made of fibers that are both good in wicking and resistant to decay are worn on the wick posts 171. In this case, the plants will grow from the wicked water and nutrients in the wicks.

As shown in FIG. 1 and FIGS. 2A-B, when the stove unit 30 is employed, the bottom of the body vessel 11 is made of thermally conductive material and is not insulated. The stove unit 30 is a wood stove which has a heat radiator 300 positioned underneath the body vessel 11 working as its support base. Preferably it is made of clay and fire brick and its side wall has an insulation outer layer 15 so that it can hold heat in high temperature for a long time to heat the body vessel 11. Preferably the stove unit 30 has the feature of secondary combustion to increase efficiency. Optionally, an auto control module may be added to control combustion according to temperatures monitored by use of mechanisms that can automatically feed fire woods into the combustion chamber and adjust the stove damper.

The chimney vent 301 of the stove unit 30 is introduced into the exhaust gas inlet 52 of the bioreactor body 10 and an duct fan may be added to drive the exhaust gases into the body vessel 11. Preferably, as shown in FIGS. 4A-B, an inline duct fan 164 is installed between the air outlet 72 of the bioreactor body 10 and the air inlet 162 of the extension 100 to drive the exhaust gases into the upper channel 101 of the extension 100 from the body vessel 11, and in the same time to create a negative pressure in the inside space of the body vessel 11 to draw flue gas from the chimney vent 301 flowing into the body vessel 11. The flue gas is "washed" by the liquid inside the middle chamber 32 and filtered by the solid wastes inside the upper chamber 31, therefore heat, particles and some volume of the flue gas are trapped inside the body vessel 11. Preferably, an air filter pad 73 is installed inside the air outlet 72 to further filter particles and water vapour so that the flowing gases inside the duct fan 164 are cleaner and with less water.

Both the exhaust gases fed into the body vessel 11 and produced from degradation of the fed wastes inside the body vessel 11 are "washed", filtered and trapped either inside the body vessel 11 or inside the wicking bed 170 with some volume of the exhaust gases exiting from the top growing media of the wicking bed 170. Preferably, the wicking bed 170 is staying inside a greenhouse so that the exhaust gases exiting from the wicking bed 170 may be further trapped for good uses, for example, to elevate the CO2 ppm into a level inside the greenhouse that can stimulate growth of plants, or to elevated the CO2 ppm into a level inside the greenhouse that can kill pests without hurting the inside growing plants.

The extension 100 and all the components inside the extension 100 and inside the body vessel 11 are made of materials that are corrosion resistant and high temperature (for example 100° C. and up) resistant. When the stove unit 30 is employed, the bottom and side walls of inner tank of the lower chamber 33 are made of steel or other metals that are treated for corrosion resistant and are high temperature (for example 800° C. and up) resistant.

The size of the bioreactor body 10 and the size of the extension 100 are proportionally arranged and dependable to the volume of biodegradable wastes to be treated. One bioreactor body 10 and one extension 100 are normally installed for one site, however it is also optional to have two or more bioreactor bodies 10 and two or more extensions 100 in one site. When two or more extensions are serially installed with one bioreactor body 10, the first extension 100 near to the bioreactor body 10 have an liquid outlet 163 in the far end chamber 182 to connect into the liquid inlet 161 of the next extension 100, and the last extension 100 far from the bioreactor body 10 have an syphon in the far end chamber 182 to let go the liquid.

Preferably, the diameter of the bioreactor body 10 and width of the extension 100 match with each other. For a wicking bed a width of 4-5 feet is good for operations if it is reachable from both sides while a width of 2-3 feet is good for operations if it is reachable from only one side.

One of the options for the heights of the body vessel 11 is in the range of 2.5 feet to 4 feet so that when the body vessel 11 sits on the stove radiator 300 the total height from top of the feed module 44 to the ground is about 4-6 feet, a proper height reachable for most persons to feed wastes.

One of the options for the heights of the extension 100 is 12 inches so that it has a height space of around 3-4 inches for both the upper channel 101 and the lower channel 103 that allows easy installation of the aeration and water pipes while it has a height space of around 4-6 inches that is good to hold enough bio-filter media.

Optionally, a thermoelectric generator module may be integrated into the stove unit 30 so that it generates electricity to power the electronic components of the stove unit and the bioreactor system from the temperature differences between the side contacting with the stove wall (a part without the insulation layer) and the opposite side.

Preferably a grinder module may be employed to grind the kind of solid wastes such as shells, bones and etc. having unbreakable residue humus into fine particles and liquids, therefore to speed the composting process and to supply bio-mineral nutrients into the integrated food growing system. Optionally, for embodiments using large size of body vessels 11, more than one feed module 44 and more than one mixing agitation modules 41 (if driven by the motor 60) may be employed in each body vessel 11.

The central control unit 20 is installed nearby the bioreactor body 10 or other places, preferably it is installed on the side wall or on the top lid 18. It reads and displays all the data from the sensors both inside the body vessel 11 and inside the extension 100. It automatically controls the mixing agitation module 41, the aeration module 42 and the heat module 43 to turn them on/off according to pre-set conditions and/or monitored data of inside conditions. Preferably, the central control unit 20 has an interface to connect into a Wi-Fi or cellular modem or other network communication system, so that the monitored data of the central control unit 20 can be reached by a specially designed application that runs on smart phones, tablets and other devices.

Preferably, the liquid inside the extension 100 is tested and monitored regularly for PH and chemical components. In certain conditions, the plants that are good to degrade the monitored chemicals by rhizofiltration and phytoremediation are employed to grow in the extension wicking bed(s).

Figure 8:
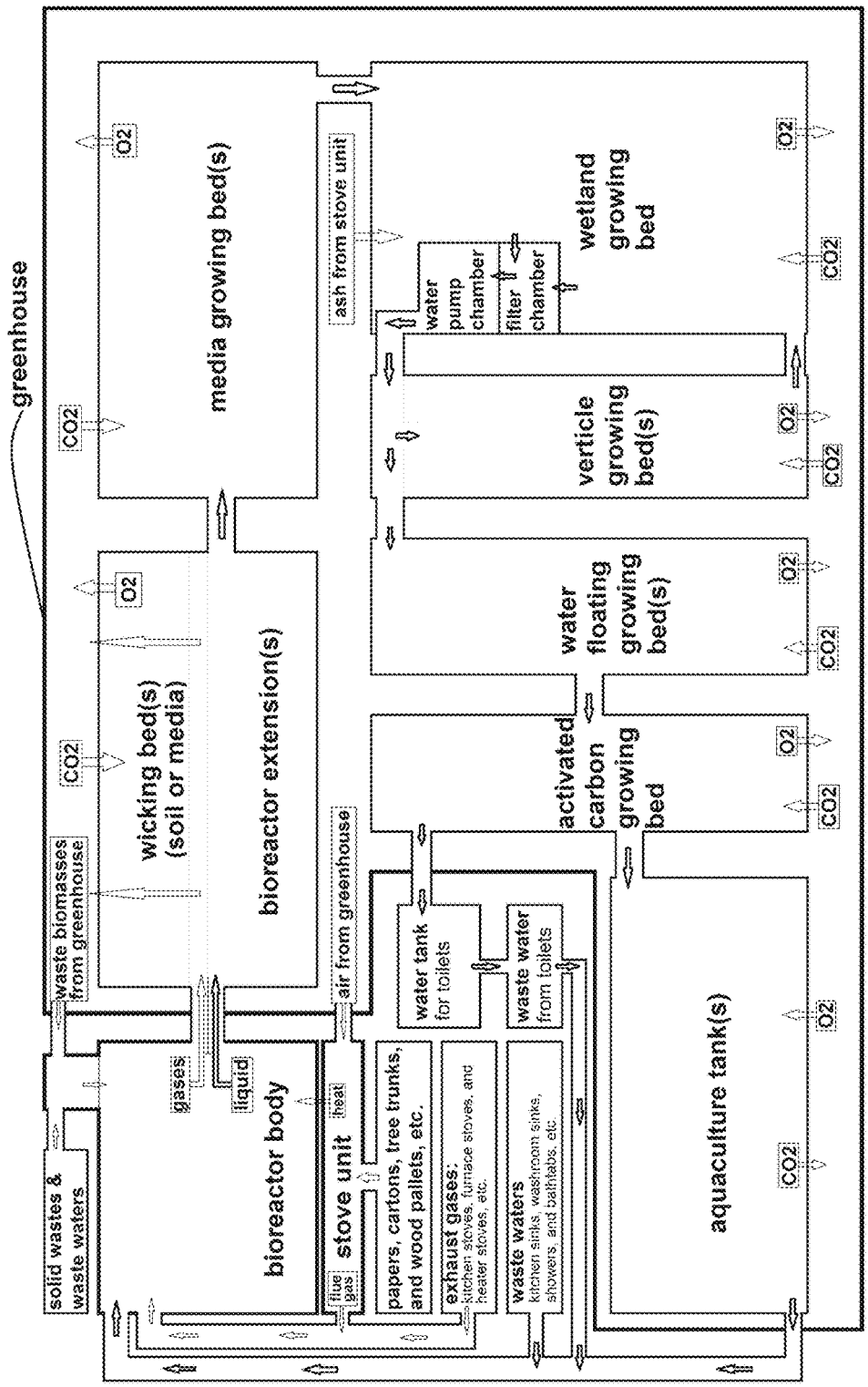
FIG. 8 shows the flow chart of both water and gases in a typical embodiment of a compoponic system.

As shown in FIG. 8, a closed-loop recirculation of both gases and water including nutrients and energy may be established in an integrated system both for growing foods and for recycling wastes based on a typical embodiment of this invention.

As shown in FIG. 8, an integrated system of a typical embodiment of this invention integrates the composting process with the aquaponic technology together and has both soil wicking growing beds and soilless hydroponic growing beds, therefore can culture most kinds of food plants. It automatically completes multiple tasks in a continuous manner. It recycles all the biodegradable wastes including solid wastes, waste waters and exhaust gases from both the system itself and the onsite human activities. It mimics nature in a wider range than the aquaponics, and recirculates nutrients, carbon and energy among human being, animals, microorganisms and plants by way of photosynthesis, slow burning by cellular respiration and burning by combustion.

It involves multidisciplinary knowledges and technologies such as composting process, hydroponics, aquaculture, biology, agriculture, mechanics, architecture, auto control and information technology, etc. It also attributes to address quite a few challenge issues such as climate change, food security, food safety, circular economy, sustainable agriculture and sustainable development, etc. A new word "compoponics" is therefore hereby created to epitomize specifications and functions of this kind of integrated system, for the word "compost" has both the meaning of decomposition and the meaning of "putting together".

As shown in FIG. 8, a typical compoponic system composes a present invention bioreactor system including a plurality of soil wicking growing beds, a plurality of aquaculture tanks, a plurality of hydroponic growing beds including media growing beds, water floating growing beds, vertical growing beds, at least one wetland growing bed, and at least one activated carbon growing bed. The activated carbon growing bed is so positioned that water from output of the activated carbon growing bed flows directly into the aquaculture tanks and into the water tank for toilets.

As shown in FIG. 8, the wetland growing bed is positioned in the lowest spot of the system lot. It has a substrate layer of limestone gravel or crashed lava stone at the bottom to settle sludge. A water pump chamber and a filter chamber filled with limestone gravel or crashed lava stone are separated inside the wetland growing bed, so that suspension particles inside the water are filtered before the water is introduced into the next hydroponic growing beds. Ash from combustion inside the stove unit may be fed into the wetland so that bio-mineral nutrients of the ash are supplied into the growing beds. Sludge from the circulating water of the system settles and degrades inside the wetland growing bed. Two kinds of water plants may grow inside the wetland growing bed, those such as algae and duckweed that can be used as feeds for aquaculture animals and are good to help degrading the organic matter inside the water, and those such as *Nelumbo nucifera* that grows well in sludge and have strong root system for rhizofiltrafion and phytoremediation while its roots are also a good food.

As shown in FIG. 8, preferably all the soil wicking growing beds and all the soilless hydroponic growing beds are inside a greenhouse and the stove unit has a vent to accept air from the greenhouse into its combustion chamber, so that growing conditions may be well controlled and a closed-loop recirculation of gases (including O2 and CO2, etc.) may be established among photosynthesis of the plants inside the greenhouse, slow burning by cellular respiration during decomposition of the biodegradable wastes and burning by combustion of the stove unit. Preferably, a CO2 sensor is installed inside the greenhouse and is connected into the central control unit, so that burning process may be adjusted according to the monitored CO2 ppm value inside the greenhouse. Therefore, burning of biodegradable wastes by the stove unit may be arranged and scheduled for either of the purposes: (1) to elevate the CO2 ppm into a level inside the greenhouse that can stimulate growth of plants, or (2) to elevate the CO2 ppm into a level inside the greenhouse that can kill pests without hurting the inside growing plants. For a compoponic system of very large size, a plurality of greenhouses or a huge greenhouse separated into a plurality of closed spaces may be employed, so that according to conditions required, different ppm levels of CO2 for each greenhouse or each greenhouse space may be arranged and scheduled while different air-recirculation flow chats among the greenhouses or greenhouse spaces may be arranged and scheduled.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A bioreactor system for recycling biodegradable wastes, comprising:
   a. a bioreactor body vessel having a vessel volume, said volume is divided into an upper chamber to receive said biodegradable wastes, a middle chamber to receive a filtered biodegradable waste generated in the upper chamber, and a lower chamber to receive a liquid waste generated in the middle chamber;
   b. a perforated plate separator to separate said upper chamber from said middle chamber and a concaved or a conical separator to separate said middle chamber from said lower chamber;
   c. a mixing agitation module having a chisel plow agitator installed in the upper chamber and an oblique cone agitator installed in the middle chamber to provide a harmonized mixing;
   d. an aeration module installed in the middle chamber, said aeration module comprises of a plurality of perforated pipes fixed on an upper surface of said concaved or conical lower separator;
   e. a heating module installed in the lower chamber to heat said liquid waste and kill pathogen microbes and weed seeds of said liquid waste;
   f. an extension having an upper volume having an inlet port to receive said liquid waste from said lower chamber, a middle volume filled with a bio-filter media, and a lower volume having a second aeration module;
   g. a plurality of inlet and outlet ports;
   h. a plurality of temperature sensors installed inside both said body vessel and said extension and connected to a central control unit, said temperature sensors generating temperature-data; and
   i. said central control unit to control said modules for heating, aeration and agitation in said system,
      whereby said system degrades said biodegradable wastes into a usable liquid in continuous manner.

2. The bioreactor system of claim 1, wherein said body vessel further having a top lid and a feed module on said top lid to feed said biodegradable wastes into said upper chamber.

3. The bioreactor system of claim 1, wherein said system further having at least one waste water liquid inlet port feeding into said upper chamber.

4. The bioreactor system of claim 1, wherein said lower chamber comprising a heating-sub-chamber, wherein said heating-sub-chamber having a heating module to heat the content of said heating-sub-chamber to kill pathogen microbes and weed seeds of a waste water flowing through said heating-sub-chamber to generate a heated waste water, and a collection chamber to collect said heated waste water from the heating-sub-chamber and to moderate the temperature of the heated waste water.

5. The bioreactor system of claim 4, wherein a temperature inside said heating-sub-chamber is between 70-100° C.

6. The bioreactor system of claim 1, wherein said oblique cone agitator in said middle chamber is made by installing a plurality of oblique cones on a circle frame or circle frames together composing horizontal and/or vertical layers of which lower layer is smaller than upper layer to fit for the concaved or conical shape of said lower separator.

7. The bioreactor system of claim 1, further having a stove unit which has a heat radiator, wherein said radiator is positioned underneath the bottom of the body vessel and also works as support base of the body vessel, wherein said stove unit is a wood stove that has a heat radiator made of clay and fire brick, and its side walls has an insulation outer layer to hold heat in high temperature for a long time to heat the body vessel.

8. The bioreactor system of claim 1, further having a stove unit to heat said body vessel and said extension by a combustion process and wherein said stove unit has a chimney vent that introduces combustion exhaust gases into an exhaust gas inlet port of the body vessel, wherein said extension further having an air inlet port to accept said combustion exhaust gases from an air outlet port of the body vessel; and whereas an inline duct fan is installed along with an air pipe between said air inlet port of the extension and said air outlet port of the body vessel, whereby said inline duct fan drives said combustion exhaust gases into the extension from the body vessel and in the same time creates a negative pressure inside the body vessel to draw said combustion exhaust gases flowing into the body vessel from said chimney vent.

9. The bioreactor system of claim 8, wherein said extension further having a plurality of wick posts on a top wall of the extension and a wicking bed filled with a limestone gravel or a crushed lava stone of 8-12 inches of thickness, whereby said limestone gravel or crushed lava stone filters and degrades said exhaust gases flowing through said wicking bed, and wherein said wick posts supply water and nutrients to plants cultured in the wicking bed.

10. The bioreactor system of claim 1, further having a plurality of sensors for humidity, oxygen, ammonia, carbon dioxide and air pressure installed inside said body vessel and connected to said central control unit, wherein said sensors generating sensor-data, and wherein said central control unit reads and displays said sensor-data and controls the mixing agitation module, the aeration module and the heating module to turn on/off according to a pre-set condition.

11. The bioreactor system of claim 1, wherein the extension further having a wicking bed filled with a soil or a compost or other media of 8-12 inches of thickness with *Eisenia fetida* and plants to be cultured in the wicking bed.

12. The bioreactor system of claim 1, wherein said perforated plate separator has a plurality of perforations, wherein each said perforation has a diameter in the range of ½-¼ inch.

13. The bioreactor system of claim 1, wherein said upper chamber having *Eisenia fetida* and *Hermetia illucens* cultured to speed up decomposition of said biodegradable wastes, and wherein said body vessel further having an output port connecting to a collection container to automatically harvest larvae of said *Hermetia illucens* escaped from said upper chamber, whereby larvae harvested is used to feed aquaculture animals of an integrated aquaponic system.

14. The bioreactor system of claim 1, wherein said bio-filter media in the extension is a lightweight expanded clay aggregate (LECA).

15. A bioreactor system for recycling biodegradable wastes, comprising:
   a. a bioreactor body vessel having a vessel volume, said volume is divided into an upper chamber to receive said biodegradable wastes, a middle chamber to receive a filtered biodegradable waste generated in the upper chamber, and a lower chamber to receive a liquid waste generated in the middle chamber;
   b. a perforated plate separator to separate said upper chamber from said middle chamber and a concaved or a conical separator to separate said middle chamber from said lower chamber;
   c. an aeration module installed for the middle chamber, said aeration module comprises of a plurality of airlift pumps to generate a swirling vortex in the middle chamber;
   d. a mixing agitation module having a chisel plow agitator installed in the upper chamber to provide a harmonized mixing, and a vortex flower turbine installed in the middle chamber and driven by said swirling vortex in the middle chamber to provide necessary torque for driving said chisel plow agitator;
   e. a heating module installed in the lower chamber to heat said liquid waste and kill pathogen microbes and weed seeds of said liquid waste;
   f. an extension having an upper volume having an inlet port to receive said liquid waste from said lower chamber, a middle volume filled with a bio-filter media, and a lower volume having a second aeration module;
   g. a plurality of inlet and outlet ports;
   h. a plurality of temperature sensors installed both inside said body vessel and inside said extension and connected into a central control unit, said temperature sensors generating temperature-data; and
   i. said central control unit to control said modules for heating, aeration and agitation in said system,
      whereby said system degrades said biodegradable wastes into a usable liquid in continuous manner.

16. The bioreactor system of claim 15, further having a vortex flower turbine installed in the middle chamber and connected into a shaft rod of said mixing agitation module, whereby said swirling vortex causes rotation of the vortex flower turbine in the middle chamber which drives to rotate the chisel plow agitator in the upper chamber, wherein said vortex flower turbine is made by fixing and folding a plurality of flower leaf blades on and around a shaft rod so that both the edges of the flower leaf blades and the channels between the flower leaf blades are in a vortex featured shape.

17. The bioreactor system of claim 16, wherein said mixing agitation module further having a coaxial gear reducer installed on said top lid of the body vessel, wherein said coaxial gear reducer is fixed and supported by a tube frame of which its lower end is fixed on said upper separator and its upper end is fixed on a lower end of said coaxial gear reducer, and two alongside coaxial shaft rods inside the body vessel of which an inner shaft rod inside said tube frame connects with both the vortex flower turbine and an input draft of the coaxial gear reducer and an outer shaft rod held by a bearing fixed on the top lid connects with both the chisel plow agitator and an output shaft of the coaxial gear reducer by way of another tube frame outside the coaxial gear reducer, whereby said coaxial gear reducer driven by the vortex flower turbine provides a reduced speed and an increased torque for driving the chisel plow agitator.

18. A bioreactor system both for recycling biodegradable wastes and for growing foods, comprising:
   a. a bioreactor system of claim 8, or a bioreactor system of claim 16;
   b. a plurality of aquaculture tanks having aquaculture animals cultured;
   c. a plurality of soil wicking growing beds having plants cultured;
   d. a plurality of soilless hydroponic growing beds including media growing beds, water floating growing beds and vertical growing beds having plants cultured;
   e. at least one activated carbon growing bed having plants cultured and filtering water for culturing aquaculture animals and for flushing toilets; and
   f. at least one wetland growing bed staying in the lowest spot of a bioreactor system lot and having plants cultured, whereby said wetland growing bed receives and degrades an ash generated from combustion of said stove unit and a sludge generated from a circulating water of said bioreactor system, and wherein said wetland growing bed has a substrate layer of limestone gravel or crushed lava stone for settling sludge, a filter chamber filled with limestone gravel or crushed lava stone for filtering suspension particles, and a water pump chamber having a water pump to transport a filtered water from said filter chamber into said hydroponic growing beds,
      whereby said bioreactor system integrates a composting process and an aquaponic technology together by a closed-loop water recirculation, and mimics nature recirculating nutrients, carbon and energy among human being, animals, microorganisms and plants by way of photosynthesis, slow burning by cellular respiration and burning by combustion.

19. The bioreactor system of claim 18, further having a greenhouse to shelter said soil wicking growing beds and said soilless hydroponic growing beds and at least one CO2 sensor installed inside said greenhouse and connected into the central control unit, whereby inside said greenhouse CO2 ppm may be elevated by combustion of the stove unit either to stimulate growth of plants or to kill pests; and wherein said greenhouse has a vent to introduce an air from said greenhouse into a combustion chamber of the stove unit, whereby said bioreactor system may establish a closed-loop recirculation of O2 and CO2 by way of photosynthesis of plants inside the greenhouse, slow burning by cellular respiration during decomposition of the biodegradable wastes and burning by combustion of the stove unit.

20. The bioreactor of claim 18, whereby a plant growing inside said wetland growing bed is *Nelumbo nucifera*.

* * * * *